United States Patent [19]
Chong et al.

[11] Patent Number: 5,510,340
[45] Date of Patent: Apr. 23, 1996

[54] ANTIHYPERCHOLESTEROLEMIC COMPOUNDS AND RELATED PHARMACEUTICAL COMPOSITIONS AND METHODS OF USE

[75] Inventors: Wesley K. M. Chong, Encinitas; Wan-Ru Chao, Sunnyvale; Dennis M. Yasuda, Campbell; John G. Johansson, Menlo Park, all of Calif.; Mitchell A. Avery, Grand Forks, N. Dak.; Masato Tanabe, Palo Alto, Calif.

[73] Assignee: SRI International, Menlo Park, Calif.

[21] Appl. No.: 898,934

[22] Filed: Jun. 12, 1992

[51] Int. Cl.$^6$ .................. C07J 71/00; A61K 31/58
[52] U.S. Cl. .................. 514/172; 514/176; 540/49; 540/50; 540/59; 540/61
[58] Field of Search .................. 514/172, 176; 540/49, 50, 59

[56] References Cited

U.S. PATENT DOCUMENTS

| | | | |
|---|---|---|---|
| 3,178,409 | 4/1969 | Gike | 260/239.5 |
| 3,542,770 | 11/1970 | Debono et al. | 540/50 |
| 4,202,891 | 3/1980 | Schroepfer, Jr. et al. | |
| 5,126,488 | 6/1992 | Johnston et al. | 540/49 |
| 5,457,097 | 10/1995 | Buzzetti et al. | 514/176 |

FOREIGN PATENT DOCUMENTS

| | | |
|---|---|---|
| 327119 | 8/1989 | European Pat. Off. |
| 335106 | 10/1989 | European Pat. Off. |

OTHER PUBLICATIONS

E. J. Parish et al., "Synthesis of 3β-Hydroxy-5α-cholest-8-en-7-one and 3β-Hydroxy-5α-cholest-8-en-11-one:Evaluation as Potential Hypocholesterolemic Agents," *Steroids: Structure, Function and Regulation*, vol. 48, No. 5–6 (1986).

R. Osawa, "Dehydration of Bile Acids and Their Derivatives. IX. Oxidation of Methyl 3α-Acetoxy-Δ$^7$-cholenate with Selenium Dioxide", *Bulletin of the Chemical Society of Japan* 35(1):158–163 (1962).

D. H. R. Barton and G. F. Laws, "Some Oxidation Products of Ergosta-7:14:22-trien-3β-yl Acetate", in *J. Chem. Soc.:* 52–63 (1954).

S. K. Erickson et al., "7-Ketocholesterol: It's Effects on Hepatic Cholesterogenesis and Its Hepatic Metabolism In Vivo and In Vitro", *J. Biol. Chem.* 252(15):5186–5193 (1977).

L. L. Frye et al., "Dual Action Inhibitors of Cholesterol Biosynthesis", Abstract 79 in *201st American Chemical Society Meeting, Medicinal Chemistry Division* (Atlanta 1991).

L. L. Frye et al., "Dual Action Inhibitors of Cholesterol Biosynthesis", Abstract 154 in *203rd American Chemical Society Meeting, Medicinal Chemistry Division* (San Francisco 1992).

H. E. Stavely et al., "Steroids with Double Bonds between Quaternary Carbon Atoms. I. The Oxidation of α-Ergostenyl Acetate", in *J. Am. Chem. Soc.* 65:1285–1289 (1943).

Primary Examiner—Nicholas Rizzo
Attorney, Agent, or Firm—Reed & Robins

[57] ABSTRACT

Novel antihypercholesterolemic agents are provided. An exemplary group of compounds has the structural formula (I)

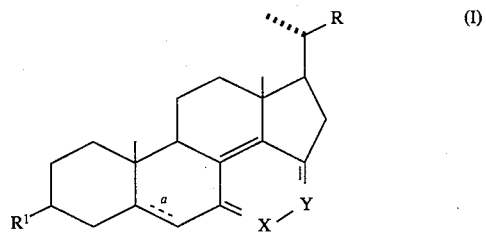

wherein R is a C-17 side chain, $R^1$ is —OH, =O, or the like, and X and Y are N, N→O, CH, C—OH, C—OCH$_3$ or C—Z. Methods of using the compound of formula (I) or other novel oxysterol analogs to treat hypercholesterolemia are provided, as are pharmaceutical compositions containing the compounds.

31 Claims, No Drawings

ANTIHYPERCHOLESTEROLEMIC COMPOUNDS AND RELATED PHARMACEUTICAL COMPOSITIONS AND METHODS OF USE

TECHNICAL FIELD

The present invention relates generally to pharmaceutical agents for lowering serum cholesterol in a hypercholesterolemic individual, and more particularly relates to novel antihypercholesterolemic compounds. The invention also relates to methods and pharmaceutical compositions for treating hypercholesterolemic individuals.

BACKGROUND

Atherosclerosis is a condition in which abnormal amounts of lipids are deposited in certain arteries, resulting in intimal thickening. The condition manifests itself by circulatory occlusion, principally of the coronary, cerebral and peripheral arteries. Ensuing complications can lead to coronary heart disease, cerebrovascular disease, and some forms of peripheral vascular disease. These conditions are the major causes of death in the United States. It has long been known that there is a relationship between atherosclerosis and high levels of plasma lipids, particularly cholesterol. In fact, hypercholesterolemia is a primary risk factor for coronary heart disease. In humans, more than one-half of total body cholesterol is derived from de novo synthesis.

Many individuals can lower their elevated cholesterol levels by dietary management of the amounts of cholesterol and fat they ingest. However, for patients who require therapeutic intervention for proper management of their serum cholesterol levels, only a few drugs are available, and many of these patients are unable to use these drugs because of the attendant side effects. There is accordingly a need in the art for agents which can lower serum cholesterol levels without giving rise to deleterious side effects.

The present invention is addressed to the aforementioned need in the art, and is premised on the discovery that certain synthetic oxysterols are extremely useful in inhibiting the biosynthesis of cholesterol. While not wishing to be bound by theory, the inventors herein postulate that these new agents act by either inhibiting or down-regulating the levels of hydroxy-methylglutaryl-coenzyme A reductase ("HMG-CoA reductase"), or by inhibiting or down-regulating the levels of low-density lipoprotein ("LDL") receptors, or a combination thereof. The present compounds are surprisingly effective in inhibiting cholesterol biosynthesis; the compounds may also have utility as prophylactic agents for general use against atherosclerosis and coronary heart disease.

SUMMARY OF THE INVENTION

Accordingly, it is a primary object of the invention to address the above-mentioned need in the art by providing novel compounds useful as antihypercholesterolemic agents.

It is another object of the invention to provide pharmaceutical compositions for treating hypercholesterolemia.

It is a further object of the invention to provide a method for lowering serum cholesterol in a hypercholesterolemic individual.

Additional objects, advantages and novel features of the invention will be set forth in part in the description which follows, and in part will become apparent to those skilled in the art upon examination of the following, or may be learned by practice of the invention.

In a first embodiment, the invention relates to certain novel compounds which are active antihypercholesterolemic agents. The novel compounds presently disclosed and claimed possess significant oral activity and may be readily synthesized. The compounds are oxysterol analogs having the structural formula (I), (II), (III), (IV) or (V)

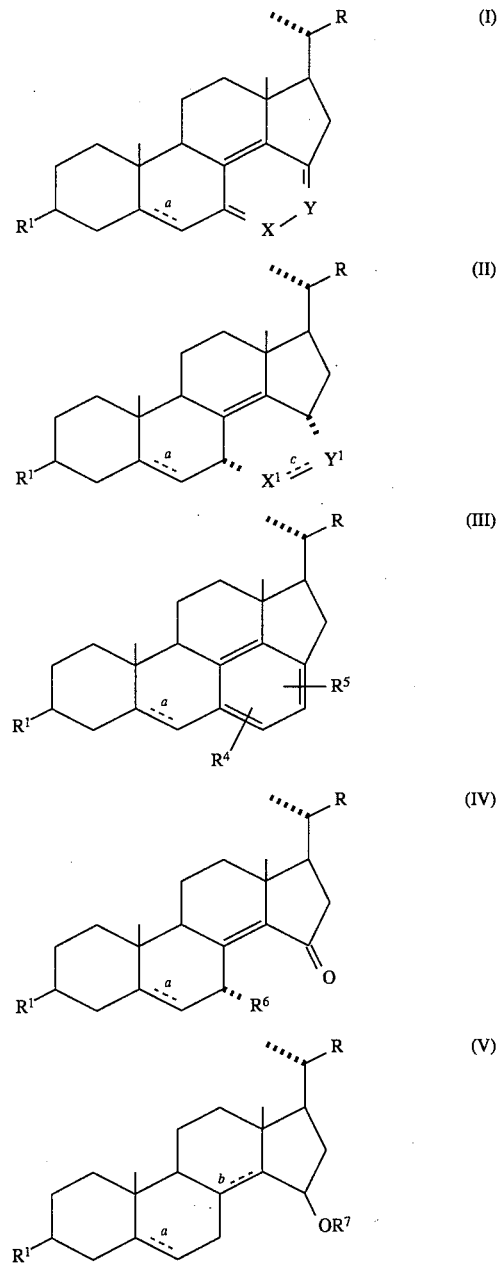

wherein R, $R^1$, $R^4$, $R^5$, $R^6$, $R^7$, X, Y $X^1$, $Y^1$, a and b are defined below.

The invention also relates to pharmaceutical compositions containing one or more of the above compounds, and further encompasses methods of treatment involving administration of one or more of the above compounds to a patient to lower serum cholesterol levels. These methods of treatment involve administration of a composition containing an oxysterol, as defined by formulae (I) through (V) above, within the context of a dosing regimen effective to achieve the intended therapeutic result.

DETAILED DESCRIPTION OF THE INVENTION

Definitions and Nomenclature:

Before the present compounds, compositions and methods are disclosed and described, it is to be understood that this invention is not limited to specific reagents or reaction conditions, specific pharmaceutical carriers, or to particular administration regimens, as such may, of course, vary. It is also to be understood that the terminology used herein is for the purpose of describing particular embodiments only and is not intended to be limiting.

It must be noted that, as used in the specification and the appended claims, the singular forms "a", "an" and "the" include plural referents unless the context clearly dictates otherwise. Thus, for example, reference to "an antihypercholesterolemic agent" includes mixtures of antihypercholesterolemic agents, reference to "a pharmaceutical carrier" includes mixtures of two or more such carriers, and the like.

In this specification and in the claims which follow, reference will be made to a number of terms which shall be defined to have the following meanings:

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein contain 1 to 12 carbon atoms. The term "lower alkyl" intends an alkyl group of one to six carbon atoms, preferably one to four carbon atoms.

The term "alkenylene" refers to a difunctional branched or unbranched hydrocarbon chain containing from 2 to 24 carbon atoms and at least one double bond. "Lower alkenylene" refers to an alkenylene group of 2 to 6, more preferably 2 to 5, carbon atoms.

The term "alkylene" as used herein refers to a difunctional saturated branched or unbranched hydrocarbon chain containing from 1 to 24 carbon atoms, and includes, for example, methylene (—CH$_2$), ethylene (—CH$_2$—CH$_2$—), propylene (—CH$_2$—CH$_2$—CH$_2$—), 2-methylpropylene [—CH$_2$— CH(CH$_3$)—CH$_2$—], hexylene [—(CH$_2$)$_6$—] and the like. "Lower alkylene" refers to an alkylene group of 1 to 6, more preferably 1 to 4, carbon atoms.

The term "aryl" as used herein refers to a monocyclic aromatic species of 5 to 7 carbon atoms, and is typically phenyl. Optionally, these groups are substituted with one to four, more preferably one to two, lower alkyl, lower alkoxy, hydroxy, and/or nitro substituents.

The term "arylene" refers to a difunctional aromatic moiety; "monocyclic arylene" refers to a phenylene group. These groups may be substituted with up to four ring substituents selected from the group consisting of —(CH$_2$)$_n$—NH$_2$, —(CH$_2$)$_n$—COOH, —NO$_2$, halogen and lower alkyl, where n is an integer in the range of 0 to 6 inclusive.

"Halo" or "halogen" refers to fluoro, chloro, bromo or iodo, and usually relates to halo substitution for a hydrogen atom in an organic compound. Of the halos, chloro and fluoro are generally preferred.

The term "oxysterol analog" as used herein to describe the compounds of the invention refers to compounds encompassed by structural formulae (I), (II), (III), (IV) or (V).

"Optional" or "optionally" means that the subsequently described event or circumstance may or may not occur, and that the description includes instances where said event or circumstance occurs and instances where it does not. For example, the phrase "optionally substituted phenyl" means that the phenyl may or may not be substituted and that the description includes both unsubstituted phenyl and phenyl where there is substitution. Also, a dotted line adjacent an unbroken line which is stated to indicate an "optional double bond" means that a double bond may or may not be present (and if not present, that the adjacent atoms are covalently bound via a single bond).

By the term "effective amount" of an agent as provided herein is meant a nontoxic but sufficient amount of the agent to provide the desired lowering of serum cholesterol. As will be pointed out below, the exact amount required will vary from subject to subject, depending on the species, age, and general condition of the subject, the severity of the hypercholesterolemia, the particular antihypercholesterolemic agent and its mode of administration, and the like. Thus, it is not possible to specify an exact "effective amount". However, an appropriate effective amount may be determined by one of ordinary skill in the art using only routine experimentation.

By "pharmaceutically acceptable" is meant a material which is not biologically or otherwise undesirable, i.e., the material may be administered to an individual along with the selected antihypercholesterolemic agent without causing any undesirable biological effects or interacting in a deleterious manner with any of the other components of the pharmaceutical composition in which it is contained.

In describing the location of groups and substituents, the following numbering systems will be employed.

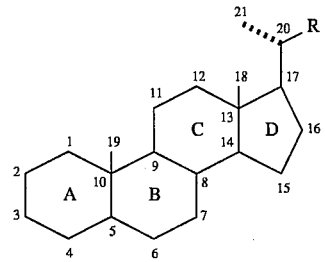

This system is intended to conform the numbering of the cyclopentanophenanthrene nucleus to the convention used by the IUPAC or Chemical Abstracts Service. The term "steroid" as used herein is intended to mean compounds having the aforementioned cyclopentanophenanthrene nucleus.

In these structures, the use of bold and dashed lines to denote particular conformation of groups again follows the IUPAC steroid-naming convention. The symbols "α" and "β" indicate the specific stereochemical configuration of a substituent at an asymmetric carbon atom in a chemical structure as drawn Thus "α" denoted by a broken line, indicates that the group in question is below the general plane of the molecule as drawn, and "β" denoted by a bold line, indicates that the group at the position in question is above the general plane of the molecule as drawn.

In addition, the five- and six-membered rings of the steroid molecule are often designated A, B, C and D as shown.

The Novel Compounds:

The novel compounds provided herein are those defined by the structural formulae (I), (II), (III), (IV) and (V) above. Turning first to structural formula (I)

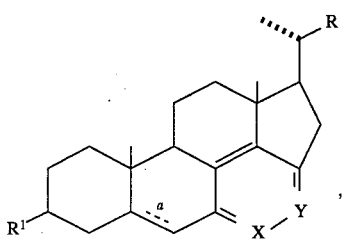

(I)

compounds encompassed by that formula have side-chains "R" selected from the group consisting of $CH_3$, $CH_2OH$, $CH_2CH_2CH_2CH(CH_3)_2$, $CH_2CH_2CH_2C(CH_3)_2$—OH, $CH_2CH_2C(CH_3)_2$—F, $CH=CH$—$CH(CH_3)$—$CH(CH_3)_2$, $CH_2CH_2CH(CH_2CH_3)CH(CH_3)_2$, and $CH=CH$—$CH(CH_2CH_3)CH(CH_3)_2$. In this group, it will be recognized that the side chain $CH_2CH_2CH_2CH(CH_3)_2$ corresponds to the side chain present in the cholesterol molecule, while the side chain $CH=CH$—$CH(CH_3)$—$CH(CH_3)_2$ corresponds to that present in the ergosterol molecule. These two side chains are preferred, with the cholesterol side chain $CH_2CH_2CH_2CH(CH_3)_2$ particularly preferred.

The $R^1$ moiety at the 3-position is selected from the group consisting of —OR, =O, —$OR^8$, —$(CO)R^9$, —$O(CO)$—$(CH_2)_n$—COOH, a sulfate group, or an Mg, Na, or K salt of a sulfate group, where $R^8$ is lower alkyl, $R^9$ is a $C_1$-$C_{20}$ aliphatic group or a phenyl group, and n is an integer in the range of 2 to 6 inclusive. Preferred $R^1$ moieties are hydroxyl and benzoate.

X and Y may be the same or different, and are selected from the group consisting of N, N→O, CH, C—OH, C—$OCH_3$ and C—Z where Z is halogen, with the proviso that at least one of X and Y is N or N→O. In preferred formula (I)-type compounds, both X and Y are N; however, when both X and Y are N, R is other than $CH=CH$—$CH(CH_3)$—$CH(CH_3)_2$. Preferred formula (I)-type compounds also include structures wherein one of X and Y is N→O.

The C-5 and C-6 carbon atoms are linked by either a single bond or a double bond; the symbol "a" thus represents an optional double bond. In preferred compounds, the bond between the 5- and 6-positions is a single bond.

With regard to the compounds of structural formula (II)

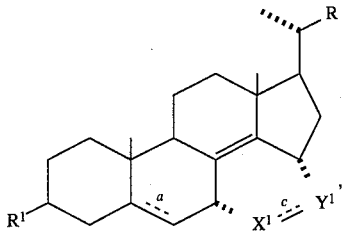

(II)

R, $R^1$ and "a" are as defined for the compounds of structural formula (I). As with the compounds of formula (I), preferred R groups are $CH_2CH_2CH_2CH(CH_3)_2$ and $CH=CH$—$CH(CH_3)$—$CH(CH_3)_2$, and preferred $R^1$ moieties are hydroxyl and benzoyl.

In the group of compounds defined by structural formula (II), the moieties $X^1$ and $Y^1$ are independently selected from the group consisting of $NR^2$, $CR^2$, O and S, where the $R^2$ may be the same or different and are selected from the group consisting of H, lower alkyl and —$COOR^3$ where $R^3$ is lower alkyl, or wherein the $R^2$ are linked together to form a —(CO)—Z—(CO)— bridge, where the "Z" linkage is alkylene, alkenylene, monocyclic arylene of 5 to 7 carbon atoms with up to four ring substituents, —S—, or —$NR^{10}$— where $R^{10}$ is H, lower alkyl or monocyclic aryl of 5 to 7 carbon atoms with up to 5 ring substituents, and wherein the ring substituents are selected from the group consisting of —$NH_2$, —COOH, —$NO_2$, halogen and lower alkyl, with the proviso that if both $X^1$ and $Y^1$ are $CR^2$, "c" represents a double bond, and that in all other cases $X^1$ and $Y^1$ are linked by a single bond.

Preferred compounds within this group are wherein $X^1$ and $Y^1$ are both N—$COOR^3$ where $R^3$ is lower alkyl. Also preferred are compounds wherein $X^1$ and $Y^1$ are both $NR^2$ and the $R^2$ are linked together to form a—(CO)—Z—(CO)— bridge where Z is phenylene, i.e., compounds having the structural formula (IIa)

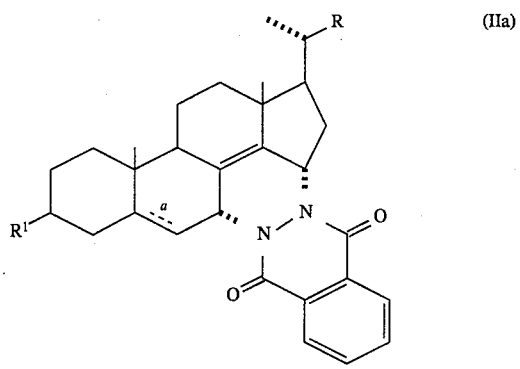

(IIa)

In the compounds encompassed by structural formula (III)

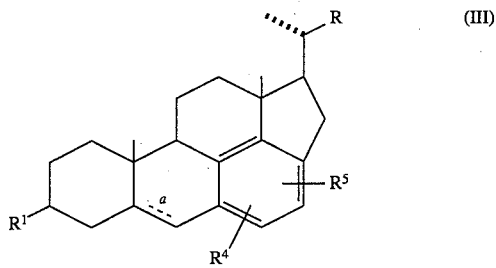

(III)

R, $R^1$ and "a" are as defined above. As with the compounds of formulae (I) and (II), preferred R groups are either $CH_2CH_2CH_2CH(CH_3)_2$ or $CH=CH$—$CH(CH_3)$—$CH(CH_3)_2$ and preferred $R^1$ moieties are hydroxyl and benzoyl.

In formula (III), $R^4$ and $R^5$ are independently selected from the group consisting of H, lower alkyl, lower acyl, lower alkoxy, —$NH_2$ and halogen, or $R^4$ and $R^5$ may be linked together to form a 5- or 6-membered aromatic or heterocyclic ring. In preferred compounds within this group, $R^4$ and $R^5$ are both hydrogen.

In the compounds encompassed by structural formula (IV)

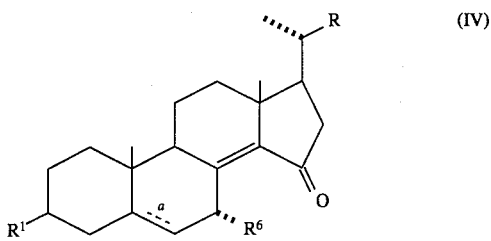

(IV)

R, $R^1$ and "a" and preferred R and $R^1$, are as given above. $R^6$ is halogen. In preferred compounds within this group, $R^6$ is fluorine.

In the compounds of formula (V),

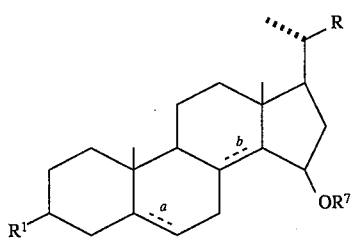

R, $R^1$ and "a" and preferred R and $R^1$, are as given above. In these structures: the symbol "b" represents an optional double bond between the C-8 and C-14 positions; and $R^7$ are selected from the group consisting of hydrogen and lower alkyl.

Utility and Administration:

The compounds of the invention defined by structural formulae (I) through (V), including the pharmacologically acceptable salts thereof, are useful as antihypercholesterolemic agents and may be conveniently formulated into pharmaceutical compositions composed of one or more of the compounds in association with a pharmaceutically acceptable carrier. Pharmaceutical compositions for lowering serum cholesterol levels may also be formulated with compounds encompassed by the structure of formula (I) but wherein both X and Y are N and the moiety "R" represents the ergosterol side chain $CH=CH-CH(CH_3)-CH(CH_3)_2$. Such compounds have been described in the literature as synthetic intermediates, but their utility as antihypercholesterolemic agents has been newly discovered by the present inventors. *Remington's Pharmaceutical Sciences*, latest edition, by E. W. Martin (Mack Publ. Co., Easton Pa.) discloses typical carriers and conventional methods of preparing pharmaceutical compositions which may be used to prepare formulations using the antihypercholesterolemic compounds of the invention.

The compounds may be administered orally, parenterally (e.g., intravenously), by intramuscular injection, or by intraperitoneal injection, or the like, although oral administration is preferred. The amount of active compound administered will, of course, be dependent on the subject being treated, the subject's weight, the manner of administration and the judgment of the prescribing physician. Generally, however, dosage will be in the range of approximately 10 mg to 200 mg/day, more typically in the range of about 50 mg to 100 mg/day.

Depending on the intended mode of administration, the pharmaceutical compositions may be in the form of solid, semi-solid or liquid dosage forms, such as, for example, tablets, suppositories, pills, capsules, powders, liquids, suspensions, or the like, preferably in unit dosage form suitable for single administration of a precise dosage. The compositions will include, as noted above, an effective amount of the selected drug in combination with a pharmaceutically acceptable carrier and, in addition, may include other medicinal agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension.

If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, referenced above.

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

Process for Preparation:

The compounds of the invention may be prepared in high yield using relatively simple, straightforward methods as exemplified in the experimental section herein.

Synthesis of representative compounds are detailed in the examples as follows: representative compounds of structural formula (I) are set forth in Examples 1 and 2; representative compounds of structural formula (II) are set forth in Examples 3–7; a representative compound of structural formula (III) is set forth in Example 8; a representative compound of structural formula (IV) is set forth in Example 9; and representative compounds of structural formula (V) are set forth in Examples 10 and 11. Side chain modifications, i.e., chemical manipulation at the C-17 position, are within the skill of the art and involve conventional techniques; exemplification of such synthetic manipulation is set forth in Example 12.

The heterocycle-fused steroids of structural formula (I) may be prepared using 7-dehydrocholesterol as a starting material, as described in Examples 1 and 2. Prior to other intramolecular conversions, the 3-OH group is protected, e.g., as a benzoyl moiety (Example 1, part (a.)); this compound is treated with an acid catalyst effective to induce isomerization to the 7,14-diene (Example 1, part (b.)). The 3-protected 7,14-diene is then converted, through a peroxide intermediate, to a 7,15-diol (Example 1, parts (c.) and (d.)). The 7,15-diol is then oxidized to a dione, which via condensation and cyclization with, e.g., hydrazine (where both "X" and "Y" are N), may be converted to a heterocycle-fused steroid such as pyridazine (Example 1, parts (e.) and (f.)). The protecting group at the 3-position may then be removed, if desired, using conventional techniques, e.g., treatment with $OH^-$ (Example 2). Example 3 illustrates the preparation of a different type of compound encompassed by structural formula (I), a heterocycle-fused steroid which is a pyridine; this involves a Diels-Alder reaction of the 7, 14-diene with toluenesulfonyl cyanide. Example 4 also relates to the preparation of a formula (I)-type compound, a heterocycle-fused pyridazine N-oxide. This reaction involves oxidation of the corresponding pyridazine compound with a suitable oxidizing agent, e.g., peracetic acid (as described in Example 4).

Compounds of formula (II) may also be prepared using 7-dehydrocholesterol as a starting material, followed by protection at the 3-OH group and isomerization to the 7,14-diene. Compounds of formula (II) may then be prepared readily via Diels-Alder cycloaddition to produce a cyclic adduct (e.g., as described in Examples 5 and 9). These cyclic adducts may then be aromatized, e.g., with dichlorodicyanobenzoquinone as described in Example 11, to produce benzenoid compounds of formula (III).

Compounds of formula (IV) may be prepared by halogenating the corresponding 7-hydroxy-15-ketone (a byproduct of the oxidation of the 7,15-diol), as described above. Halogenation may be effected, for example, with diethylaminosulfur trifluoride, as set forth in Example 12.

Compounds of formula (V) may also be prepared using the isomerized 7,14-diene as a starting material, preparing the 15-ketone therefrom, and reducing with a suitable agent (e.g., sodium borohydride, as illustrated in Example 13) to give the allylic alcohol species (Example 13) or the 15-alkoxy derivative thereof (Example 14).

Side-chain modifications, i.e., interconversion of the C-17 cholesterol side chain with a C-17 ergosterol side chain, and preparation of 25-fluoro and 25-hydroxy compounds, are readily carried out as described in Example 15.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

Experimental

The following examples are put forth so as to provide those of ordinary skill in the art with a complete disclosure and description of how to make and use the antihypercholesterolemic compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

All solvents were purchased as HPLC grade and, where appropriate, solvents and reagents were distilled from $CaH_2$ before storage over 4 Å molecular sieves. Solvent and reagent transfers were accomplished via dried syringe or cannula, and all reactions were routinely conducted under an atmosphere of argon, unless otherwise indicated. Flash chromatography was accomplished using silica gel (Kieselgel 60, 230–400 mesh), and preparative thin-layer chromatography used 1-, 1.5-, or 2-mm thick Analtech Uniplates with F-256, and 250-μ silica gel thin layer chromatography plates also purchased from Analtech. NMR analyses were conducted on either a Varian XL-400 or a JEOL FX90Q and were referenced to chloroform at δ7.27. FTIR spectra were recorded on a Perkin-Elmer 1610.

EXAMPLE 1 preparation of
Pyridazino[3',4',5',6':7,8,14,15]3β-Benzoyloxy-5α-Cholestane (12)

This example describes the preparation and characterization of a compound of (I), pyridazino [3',4',5',6':7,8,14,15] 3β-benzoyloxy-5α-cholestane (12), as illustrated in Scheme 1.

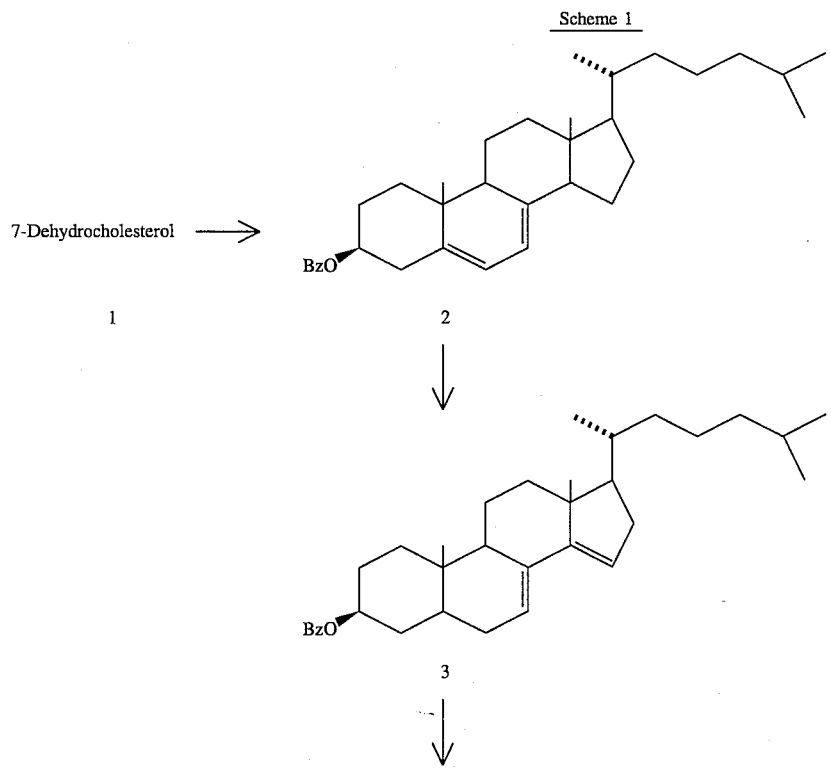

-continued
Scheme 1

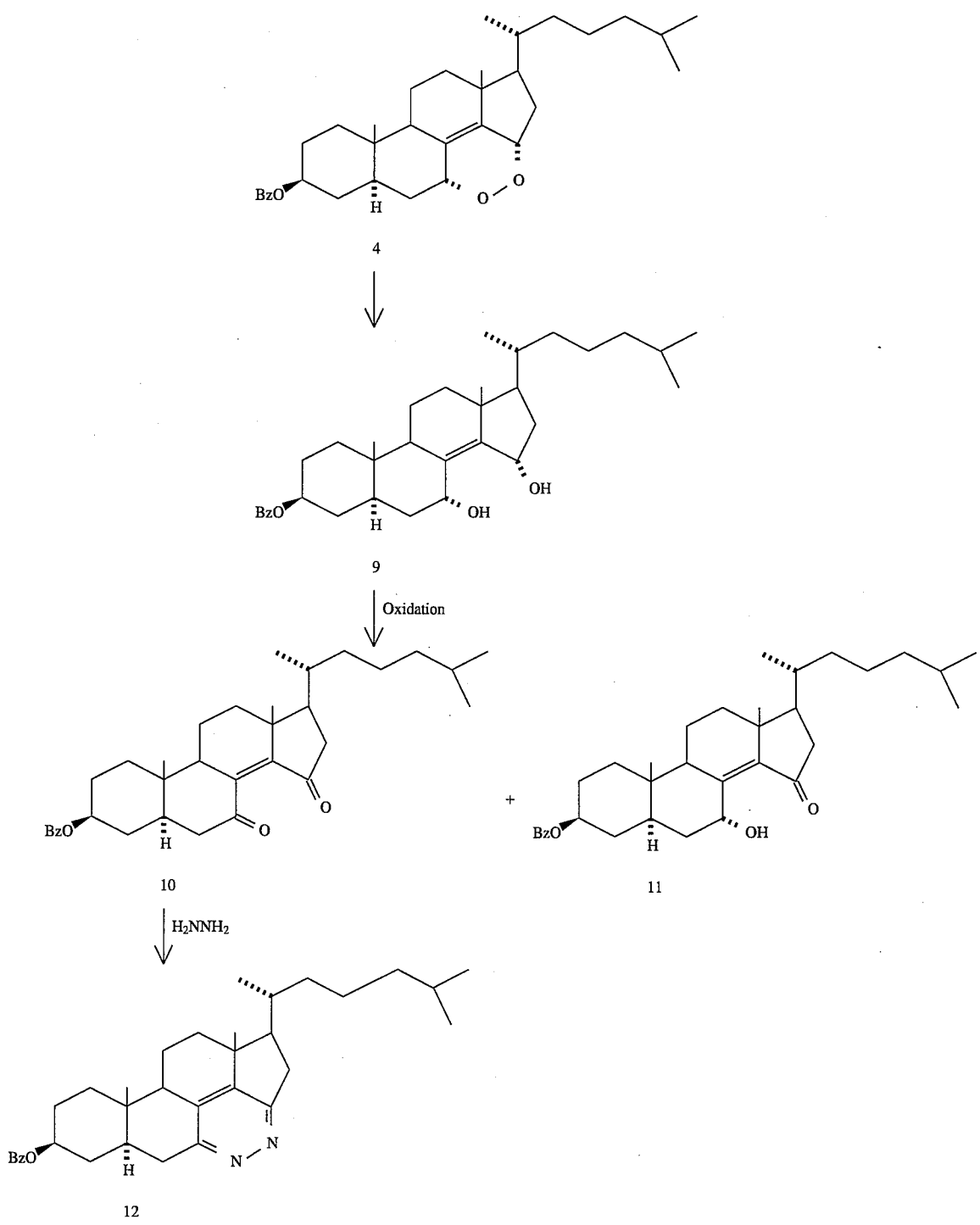

(a.) 3β-Benzoyloxycholesta-5,7-diene (2):

To a solution of 7-dehydrocholesterol (1, 50.0 g, 0.13 mol; Aldrich Chemical Co.) dissolved in dry pyridine (120 mL) was added, with stirring, benzoyl chloride (28 mL, 34.1 g, 0.24 mol). After the addition, the reaction mixture was heated at reflux for 5 min and was then left at ambient temperature for 20 min. The reaction mixture was poured with stirring into ice water (1.5 L). The precipitate was allowed to rest for 1 h and was then taken up on a filter and washed successively with water (350 mL), 5% sodium bicarbonate (200 mL), water (350 mL) and finally acetone (5×25 mL). The crude material was air dried and subsequently recrystallized. The crude material was dissolved in hot chloroform (100 mL) and to this solution was added acetone (250 mL). The flask was left at ambient temperature and then at −20° C. overnight. The crystalline material was collected by filtration, and then washed with a small amount of acetone. Total yield compound 2 after drying, 58.3 g (92%). Melting point and spectral data agree with previous reported values (Wilson et al., *J. Org. Chem.* 53:1713 (1988)).

(b.) 3β-Benzoyloxy-5α-cholesta-7,14-diene (3):

Into a stirred solution of 2 (50.0 g, 0.10 mol) in a mixture of chloroform (240 mL) and dichloromethane (60 mL) cooled to −55° C. was added a saturated solution of HCl gas in chloroform (75 mL, −55° C.). This reaction mixture was stirred at −55° C. and a stream of dry HCl gas was introduced into the mixture for 20 min. During the reaction period, the reaction mixture turned red-purple. The HCl addition was stopped and the reaction mixture was stirred at −65° C. for 1.25 h. TLC on a silver nitrate-impregnated plate and developed with a mixture of toluene/hexane (1:1) showed mainly 1 spot. The reaction flask was evacuated with a water aspirator to eliminate excess HCl. After 1 h, most HCl had evaporated and the reaction mixture was poured into a slurry of ice (200 g) and concentrated ammonium hydroxide (40 mL). The reaction mixture was transferred to a separatory funnel. The water phase was discarded and the organic phase was washed twice with water. The organic phase was poured into pyridine (11 mL) to insure that the solution did not become acidic. Evaporation of the solvent under vacuum gave a crystalline residue that was recrystallized from chloroform/acetone. The formed crystalline product 3 was taken up on a filter and washed with a small amount of acetone. Yield, 31.9 g (64%). NMR studies of this material are in agreement with published data and contain at the most 13% of material. This material is well suited for more experiments without further purification.

(c.) Photooxygenation of 3β-benzoyloxy-5α-cholesta-7,14-diene (3):

A solution of the diene (3, 2.0 g, 4.1 mmol) and eosin Y (0.1 g) in benzene (130 mL), EtOH (130 mL), and pyridine (0.1 mL) in a Pyrex flask was irradiated with three GE 12-watt ring fluorescent lamps as an external light source. Oxygen was bubbled through the stirred mixture at ambient temperature. After 5 h the solvent was evaporated and the residue was purified by flask column chromatography on 25 g of silica gel (230–400 mesh) and eluted with $Et_2O$/benzene (0:100) to (15:85) to give the following order of eluted products. The least polar material amounted to 219 mg, which was a mixture of starting material and isomeric dienes.

The second material was 3β-benzoyloxy-7α,15α-epidioxy-5α-cholest-8(14)-ene (4): 954 mg (45%), mp 75°–78° C. IR (Nujol): 1718, 1602, 1274, 1114 $cm^{-1}$. EIMS (m/z): 520 (M+), 505 (M-Me). $^1H$ NMR: δ8.04 (d, 2H, J=7.5 Hz), 7.55 (dd, 1H, 7.4, 7.4 Hz), 7.44 (dd, 2H, J=7.6, 7.6 Hz), 4.96 (m, 1H), 4.90 (m, 1H), 4.57 (m, 1H), 0.92 (d, 3H, J=6.4 Hz), 0.87 (d, 6H, J=6.7 Hz), 0.79 (s, 3H).

The third material was 3β-benzoyloxy-7α,8α-epoxy-5α-cholest-15-one (5): 121 mg (6%), mp 187°–188° C. ($CH_2Cl_2$-MeOH). IR: 1734, 1712, 1278, 1118 $cm^{-1}$. EIMS (m/z): 520 (M+) 505 (M-Me). $^1H$ NMR: δ8.02 (d, 2H, J=8.5 Hz), 7.55 (dd, 1H, J=7.4, 7.4 Hz), 7.43 (dd, 2H, J=7.4, 7.9 Hz), 4.88 (m, 1H), 3.17 (dd, 1H, J=1.1, 1.6 Hz), 2.45 (dd, 1H, J=8.6, 8.8 Hz), 1.02 (d, 3H, J=6.6 Hz), 0.96 (s, 3H), 0.87 (d, 6H, J=6.7 Hz), 0.80 (s, 3H).

The fourth material was 3β-benzoyloxy-7α,8α:14α,15α-bisepoxy-5α-cholestane (6): 104 mg (5%), mp 197°–199° C. ($CH_2Cl_2$-MeOH). IR: 1714, 1602, 1275, 1116 $cm^{-1}$. $^1H$ NMR: δ8.03 (d, 2H, J=8.4 Hz), 7.54 (dd, 1H, J=7.4, 7.4 Hz), 7.43 (dd, 2H, J=7.3, 7.9 Hz), 4.90 (m, 1H), 3.28 (s, 1H), 3.13 (broad s, 1H), 2.11 (dd, 1H, J=5.5, 5.5 Hz), 0.98 (s, 3H), 0.90 (s, 3H), 0.87 (d, 3H, J=5.9 Hz), 0.86 (d, 6H, J=6.6 Hz).

The fifth material isolated was 3β-benzoyloxy-5α-cholest-8(14)-en-15α-ol-7-one (7): 91 mg (4%), mp 157°–158° C. ($CH_2Cl_2$-EtOAc). IR (Nujol): 3398, 1718, 1665, 1600, 1272, 1114 $cm^{-1}$. EIMS (m/z): 520 (M+), 505 (M-Me). $^1H$ NMR: δ8.04 (d, 2H, J=8.4 Hz), 7.57 (dd, 1H, J=7.4, 7.4 Hz), 7.44 (dd, 2H, J=7.4, 8.0 Hz), 5.20 (broad s, 1H, exchangeable), 5.0 (m, 1H), 4.55 (d, 1H, J=6 Hz), 0.98 (d, 3H, J=6.4 Hz), 0.98 (s, 3H), 0.93 (s, 3H), 0.87 (d, 6H, J=6.4 Hz). Anal. ($C_{34}H_{48}O_4$): C,H.

The sixth material eluted was 3β-benzoyloxy-5α-cholest-8(14)-en-7α-ol-15one (8): 45 mg (2%), mp. 167°–169° C. ($Et_2O$-Hexane). EIMS (m/z): 520 (M+), 505 (M-Me). $^1H$ NMR: δ8.04 (d, 2H, J=8.5 Hz), 7.54 (dd, 1H, J=7.4, 7.4 Hz), 7.43 (dd, 2H, J=7.4, 7.9 Hz), 5.91 (dd, 1H, J=2.9 Hz), 5.0 (m, 1H), 1.02 (d, 3H, J=6.4 Hz), 1.00 (s, 3H), 0.87 (d, 6H, J=6.6 Hz), 0.77 (s, 3H). IR (Nujol): 3414, 1718, 1628, 1274, 1115 $cm^{-1}$.

(d.) 3β-Benzoyloxy-5α-cholest-8(14)-ene-7α,15α-diol (9):

To 3β-benzoyloxy-7α,15α-epidioxy-5α-cholest-8(14)-ene (4; 0.10 g, 0.19 mmol) in acetic acid (4 mL) was added zinc dust (0.06 g, 0.92 mmol) and the mixture was stirred at ambient temperature for 2 h. The zinc was filtered off and the solvent evaporated. The residue was treated with EtOAc (30 mL) and made alkaline with a saturated $NaHCO_3$ solution (30 mL). The organic layer was separated, washed with water (30 mL), dried over $MgSO_4$, filtered, and evaporated to yield 68 mg (68%) of diol 9, which crystallized from EtOAc, mp 178°–179° C. $^1H$ NMR: δ8.04 (d, 2H, J=8.5 Hz), 7.54 (dd, 1H, J=7.4, 7.4 Hz), 7.43 (dd, 2H, J=7.4, 7.8 Hz), 5.00 (m, 1H), 4.90 (d, 1H, J=5.8 Hz), 4.59 (dd, 1H, J=2.2, 2.4 Hz), 2.27 (dd, 1H, J=7.6, 7.9 Hz), 0.97 (d, 3H, J=6.4 Hz), 0.88 (d, 6H, J=6.7 Hz), 0.84 (s, 3H), 0.79 (s, 3H). IR ($CHCl_3$): 3474, 1709, 1602, 1279, 1118 $cm^{-1}$. Anal. ($C_{34}H_{50}O_4$): C, H.

(e.) 3β-Benzoyloxy-5α-cholest-8(14)-ene-7,15-dione (10): To a solution of 3β-benzoyloxy-5α-cholest-8(14)-ene-7α,15α-diol (9; 34 mg, 0.065 mmol) in acetone (3 mL) submerged in an ice bath was added Jones Reagent (0.06 mL) until the brown color persisted. After stirring for 20 min, the mixture was treated with $NaHCO_3$ (1 g) and the solvent was evaporated under reduced pressure. The residue was treated with ether (50 mL) and saturated $NaHCO_3$ solution (50 mL). The organic layer was separated, washed with water (30 mL), dried over $MgSO_4$, filtered, and evaporated to obtain 26 mg of residue, which contained two products. Purification by preparative TLC using $Et_2O$/benzene (15:85) gave 9 mg (26%) of 3β-benzoyloxy-5α-cholest-8(14)-ene-7,15-dione (10). $^1H$ NMR: δ8.03 (d, 2H, J=8.4 Hz), 7.56 (dd, 1H, J=7.4, 7.4 Hz), 7.44 (dd, 2H, J=7.4, 7.9 Hz), 4.98 (m, 1H), 2.55 (dd, 1H, J=13.9, 13.9 Hz), 2.53 (dd, 1H, J=8.3, 19.2 Hz), 2.39 (dd, 1H, J=3.5, 13.9 Hz), 2.18 (dd, 1H, J=7.0, 10.1 Hz), 2.12 (ddd, 1H, J=3.5, 3.5, 12.9 Hz), 2.08 (m, 1H), 2.01 (dd, 1H, J=11.5, 19.2 Hz), 1.02 (s, 3H), 1.01 (d, 3H, J=6.7 Hz), 1.01 (s, 3H), 0.87 (d, 6H, J=6.6 Hz). IR (Nujol): 1717, 1700, 1644, 1600, 1376, 1267, 1115 $cm^{-1}$. EIMS (m/z): 518 (M+), 503 (M-Me).

The second more polar spot in the preparative TLC was 3 mg (9%) of 3β-benzoyloxy-5α-cholest-8(14)-en-7α-ol-15-one (11). IR (Nujol): 3415, 1718, 1628, 1272, 1114 $cm^{-1}$. This compound was used to prepare 3β-benzoyloxy-7α-fluoro-5α-cholest-8(14)-en-15-one as described in Example 9, below.

(f.) Pyridazino[3',4',5',6':7,8,14,15]3β-benzoyloxy-5a-cholestane (12):

To 3β-benzoyloxy-5α-cholest-8(14)-ene-7,15-dione 10 (180 mg, 0.35 mmol) dissolved in ethanol (14 mL) was added anhydrous hydrazine (12 μl, 0.38 mmol) and the mixture was heated to 90° C. for 0.75 h. The solvent was evaporated under reduced pressure and the residue was purified by flash column chromatography on 4 g of silica gel 60 using EtOAc/CHCl₃ (4:6) yielding 127 mg (71%) of pyridazine 12, which crystallized from CH₂Cl₂/EtOAc, mp 215°–216° C. ¹H NMR: δ8.06 (d, 2H, J=8.2 Hz) , 7.57 (dd, 1H, J=7.4, 7.4 Hz), 7.45 (dd, 2H, J=7.5, 7.8 Hz), 5.09 (m, 1H), 3.18 (dd, 1H, J=5.5, 17.9 Hz), 3.11 (dd, 1H, J=6.9, 16.3 Hz), 2.96 (dd, 1H, J=10.8, 16.3 Hz), 2.64 (dd, 1H, J=12.6, 17.9 Hz), 2.34 (dd, 1H, J=5.7, 10.9 Hz), 2.25 (ddd, 1H, J=2.9, 3.5, 13.1 Hz), 2.05–2.14 (m, 2H), 1.07 (s, 3H), 1.00 (d, 3H, J=6.3 Hz), 0.89 (d, 6H, J=6.6 Hz), 0.87 (s, 3H). IR (Nujol): 1715, 1602, 1318, 1276, 1116 cm⁻¹. Anal. (C₃₄H₄₆N₂O₂): C, H.

EXAMPLE 2

Preparation of Pyridazino[3',4',5',6':7,8,14,15] 5α-Cholestan,3α-ol (13)

This example describes the preparation and characterization of a second compound of formula (I), pyridazino[3',4',5',6':7,8,14,15]5α-cholestan-3β-ol (13), as illustrated in Scheme 2.

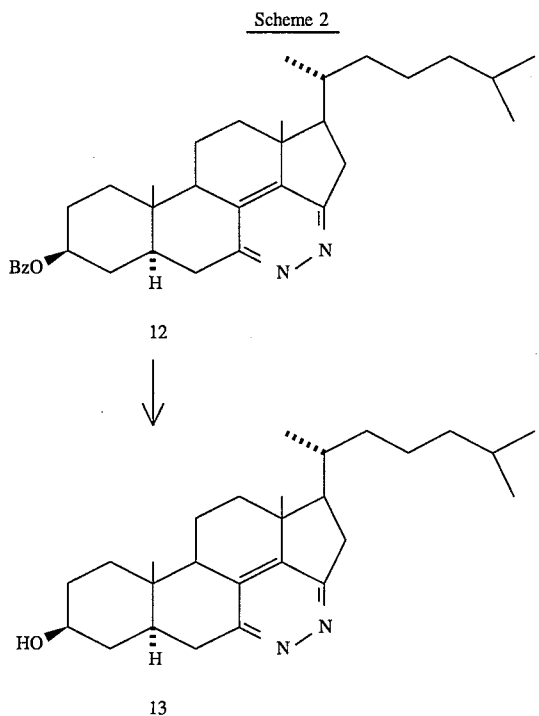

A solution of pyridazine 12 (113 mg, 0.22 mmol) in THF (1 mL) and MeOH (2 mL) was treated with 1M NaOH (0.29 mL, 0.29 mmol) and allowed to stand at ambient temperature for 16 h. The solvent was evaporated at reduced pressure and the residue was treated with CH₂Cl₂ (50 mL) and a 10% Na₂CO₃ solution (20 mL). The organic layer was separated, dried over MgSO₄, filtered, and evaporated to dryness. The residue was purified by flash chromatography on 4 g of silica gel 60 using MeOH/CHCl₃ (5:95) giving 65 mg (72%) of 13, which crystallized from CH₂Cl₂/acetone, mp 203°–205° C. ¹H NMR: δ3.71 (m, 1H), 3.13 (dd, 1H, J=5.6, 13.4 Hz), 3.10 (dd, 1H, J=6.8, 16.5 Hz), 2.95 (dd, 1H, J=10.6, 16.3 Hz), 2.61 (dd, 1H, J=12.8, 17.9 Hz), 2.27 (dd, 1H, J=6.1, 11.0 Hz), 2.23 (ddd, 1H, J=3.6, 3.6, 13.4 Hz), 1.06 (s, 3H), 0.99 (d, 3H, J=6.2 Hz), 0.89 (d, 6H, J=6.6 Hz), 0.80 (s, 3H). IR (Nujol): 3301, 1626, 1554, 1035 cm⁻¹. EIMS (m/z): 410 (M⁺), 395 (M-Me). Anal. (C₂₇H₄₂N₂O): C, H, N.

EXAMPLE 3

Preparation of Pyridino[2',3',4',5':7,8,14,15]Cholestan-3β-ol (15)

This example describes the preparation and characterization of a third compound of formula (I), pyridino[2',3',4',5':7,8,14,15]cholestan-3β-ol (15), as illustrated in Scheme 3.

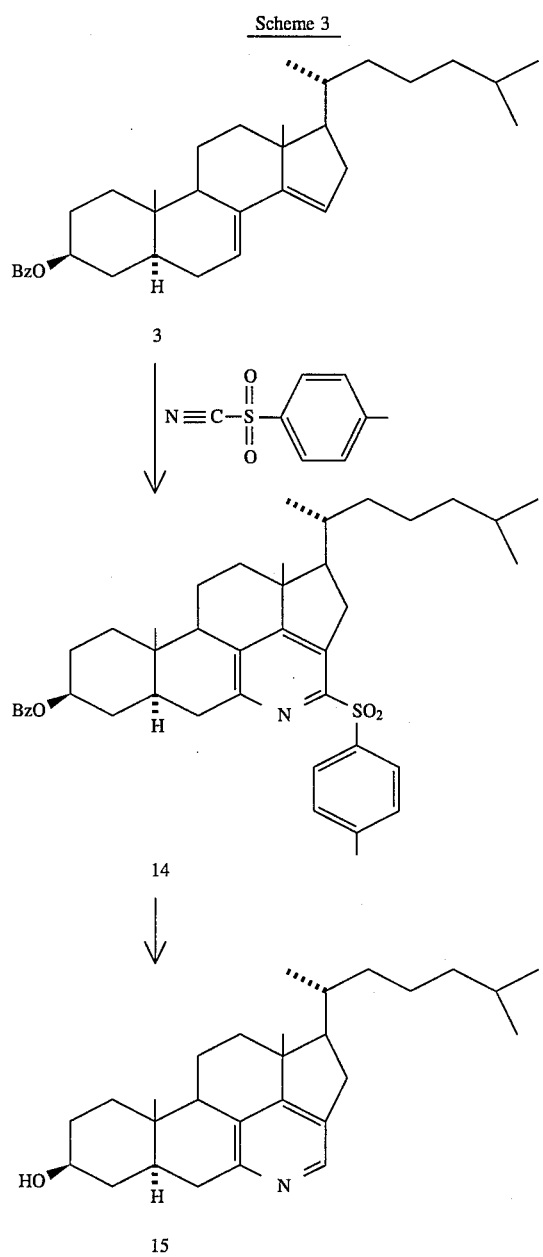

(a.) 3β-Benzoyloxy-6'-toluenesulfonylpyridino-[2',3',4',5':7,8,14,15]-cholestane:

To a solution of 3β-benzoyloxycholesta-7,14-diene (3, 2.00 g, 4.10 mmol) in dry benzene (20 mL) was added toluenesulfonyl cyanide (1.20 g, 6.62 mmol). After 20 h at ambient temperature, the mixture was heated at reflux for 4 h; then more toluenesulfonyl cyanide (1.00 g) was added, and reflux continued for another 2 h. The resultant mixture was allowed to cool, stirred with saturated aqueous NaHCO$_3$ (25 mL) and H$_2$O (25 mL), and extracted with CHCl$_3$ (40 mL). The organic layer was separated, washed with saturated aqueous NaHCO$_3$ (25 mL) and H$_2$O (25 mL), dried over Na$_2$SO$_4$, and concentrated in vacuo to a yellow oil, which was purified via flash column chromatography with silica gel (10% EtOAc/hexane) to give recovered starting material, 0.72 g, product yellow foam, 0.75 g, and pyridine 14 as white crystals, 190 mg (7%). An analytical sample was furnished by recrystallization from EtOAc/hexane as white needles, mp>245° C. $^1$H NMR (300 MHz): δ8.05 (dd, 1H, J=1.4, 8.3 Hz), 7.94 (d, 1H, J=8.3 Hz), 7.56 (dddd, 1H, J=1.3, 1.3, 6.5, 6.5 Hz), 7.43 (ddd, 1H, J=0.9, 7.6, 7.6 Hz), 7.30 (d, 1H, J=7.9 Hz), 5.00 (ddd, 1H, J=4.6, 6.6, 15.9 Hz), 3.49 (d, 1H, J=5.5 Hz), 3.43 (d, 1H, J=6.3 Hz), 3.05 (d, 1H, J=9.5 Hz), 2.98 (dd, 1H, J=9.5, 17.1 Hz), 2.53 (dd, 1H, J=12.2, 18.2 Hz), 2.42 (s, 3H), 2.35 (dd, 1H, J=7.4, 9.9 Hz), 2.23 (ddd, 1H, J=2.6, 2.6, 12.7 Hz), 1.00 (d, 3H, J=6.5 Hz), 0.98 (s, 3H), 0.92 (s, 3H), 0.83 (s, 3H). IR: 2948, 1714, 1319, 1274, 1147 cm$^{-1}$. CIMS (NH$_3$): m/e (rel int) 668 (M+H, 33) 175 (55), 158 (100). Anal. Calcd. for C$_{42}$H$_{53}$NO$_4$S: C, 75.52; H, 8.00; N, 2.10; S, 4.80. Found: C, 75.66; H, 8.20; N, 2.12; S, 4.90.

(b.) Pyridino [2',3',4',5':7,8,14,15]cholestan-3β-ol:

An admixture of mercury (0.144 mL, 1.96 g, 9.8 mmol) and sodium spheres (0.11 g, 4.6 mmol) was heated with a heat gun under argon until a violent exothermic reaction was produced, whereupon uniform amalgam resulted. The amalgam was allowed to cool to ambient temperature, and a solution of sulfone 14 (67 mg, 0.10 mmol), in dry methano (2 mL) and THF (3 mL) was added. After 10 min, a solution of methanol (2 mL) and water (2 mL) was carefully added. After 14 h at ambient temperature, the mixture was placed in a separatory funnel and the mercury was separated. The resultant mixture was acidified with 10% aqueous HCl (~1 mL), diluted with saturated aqueous NaHCO$_3$ (10 mL), and extracted with CH$_2$Cl$_2$ (3×10 mL). The combined organic layers were washed with H$_2$O, dried over Na$_2$SO$_4$, and concentrated in vacuo to a yellow oil, which was purified via flash column chromatography with silica gel (10% MeOH/CHCl$_3$) to provide a single regioisomeric pyridine 15 as a white amorphous solid, 37 mg (90%). An analytical sample was furnished by recrystallization from CH$_2$Cl$_2$/hexane as white crystals, mp 177°–178° C. $^1$H NMR (300 MHz): δ8.10 (br s, 1H), 3.68 (dddd, 1H, J=4.5, 4.5, 6.6, 11.0 Hz), 2.90 (dd, 1H, J=5.5, 9.3 Hz), 2.84 (dd, 2H, J=6.9, 6.9 Hz), 2.67 (dd, 1H, J=9.4, 15.2 Hz), 2.50 (dd, 1H, J=12.1, 17.1 Hz), 2.35 (t, 1H, J=8.5 Hz), 2.19 (ddd, 1H, J=3.3, 3.3, 12.6 Hz) , 0.99 (s, 3H), 0.98 (d, 3H, J=6.2 Hz), 0.89 (s, 3H), 0.87 (s, 3H), 0.80 (s, 3H). CIMS (NH$_3$): m/e (rel int) 603 (M+NH$_4$, 100), 464 (53). Anal. Calcd. for C$_{28}$H$_{43}$NO.H$_2$O: C, 80.33; H, 10.59; N, 3.35. Found: C, 80.74; H, 10.65; N, 3.27.

EXAMPLE 4

Preparation of Pyridazino[3',4',5',6':7,8,14,15]5α-Cholestan-3β-ol-1'-Oxide (16)

This example describes the preparation and characterization of another formula (I)-type compound, pyridazino[3',4',5',6':7,8,14,15]5α-cholestan-3β-ol-1' -oxide (16) as illustrated in Scheme 4.

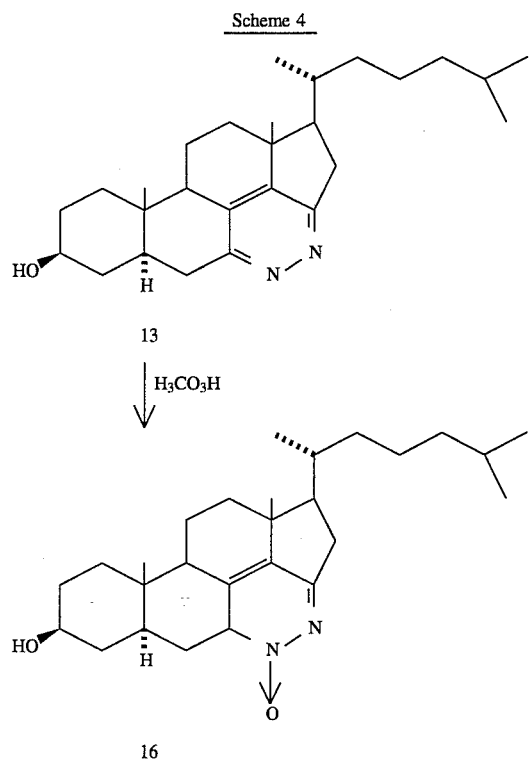

Scheme 4

A solution of pyridazine 13 (360 mg, 0.88 mmol) in CH$_2$C$_2$ (36 mL) was treated with Na$_2$CO$_3$ (0.90 g, 0.85 mmol) followed by a mixture of 32% by weight peracetic acid (0.48 mL, 2.3 mmol) in CH$_2$Cl$_2$ (15 mL) containing solid NaOAc.3 H$_2$O (63 mg, 0.46 mmol). The mixture was stirred at ambient temperature for 3 h. The reaction mixture was diluted with CH$_2$Cl$_2$ (30 mL) and washed with 10% NaHSO$_3$ (30 mL), then with saturated NaHCO$_3$ (60 mL), and finally with saturated NaCl (60 mL). The organic phase was dried over MgSO$_4$, filtered, and evaporated under reduced pressure, leaving 325 mg of yellow solid, which was a mixture of a less polar N-oxide (40%; this was the 2'-oxide) and a more polar N-oxide (60%; this was the 1'-oxide) using the TLC system acetone/CHCl$_3$ (1:1) and NMR to determine the percentages. After flash column chromatography on Merck grade 60 silica gel using the solvent acetone/CHCl$_3$ (3:7), 66 mg (18%) of the more polar N-oxide 16 was produced crystallized from acetone, mp 238°–240° C. IR (Nujol): 3263, 1572, 1088, 1042 cm$^{-1}$. EIMS (m/z): 427 (M+H). $^1$H NMR (acetone-d$_6$): δ3.58 (m, 1H), 1.10 (s, 3H), 1.02 (d, 3H, J=6.4 Hz), 0.88 (d, 6H, J=6.6 Hz), 0.76 (s, 3H).

EXAMPLE 5

Preparation of 3-benzoyloxy-7β,15βH-pyridazino [3',4',5',6':7,8,14,15]-1',2'bis(carboethoxy)-5α-cholest-3β-ol (17)

This example describes the preparation and characterization of a compound of formula (II), 3 -benzoyloxy-7β,15βH-pyridazino[3',4',5',6':7,8,14,15]-1',2'bis(carboethoxy)-5α-cholest-3β-ol (17), as illustrated in Scheme 5.

Scheme 5

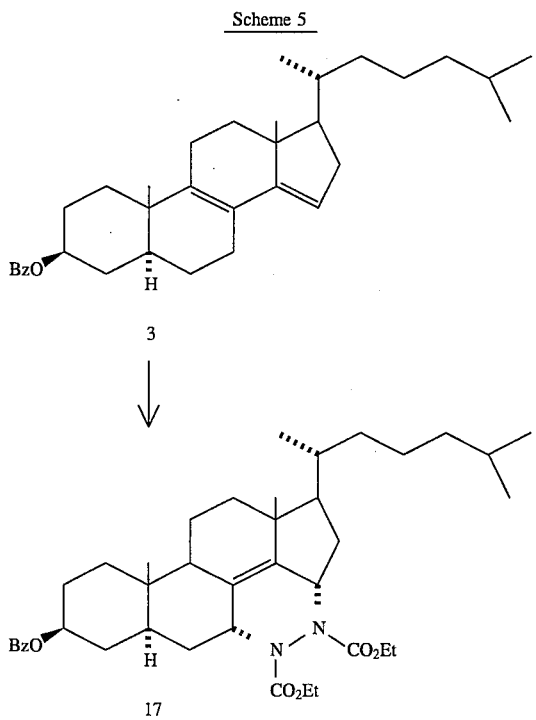

Scheme 6

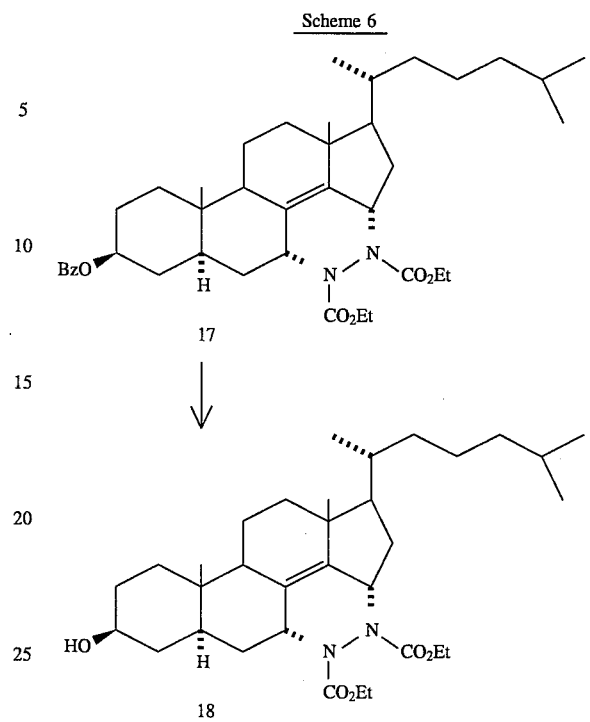

To 3β-benzoyloxy-5α-cholesta-7,14-diene 3 (9.76 g, 20.0 mmol), dissolved in benzene, was added diethylazodicarboxylate (4.0 g, 23.0 mmol) and the reaction mixture was stirred at ambient temperature for 16 h. TLC with ethyl acetate/hexane showed only traces of starting material. The solvent was evaporated in vacuo to give a thick yellow syrup. The crude material was purified on a silica gel column (7.5×30 cm) and eluted with a mixture of ethyl acetate/hexane (15:85). Yield of pure cycloadduct 17, 11.0 g (83%). $^1$H NMR: δ 8.05–7.41 (aromatic, 5H), 5.04–4.94 (m, 1H), 4.54–4.46 (m, 1H), 4.31–4.07 (m, 4H), 3.61 (d, 1H, J=11.4 Hz), 2.38–2.29 (m, 1H), 0.97 (s, 3H), 0.89 (d, 3H, J=6.5 Hz), 0.87 (s, 3H), 0.85 (s, 3H), 0.70 (s, 3H). IR: 3318, 1716, 1602, 1584, 1273, 1174, 1112 cm$^{-1}$. EIMS (m/z): 662.

To benzoate 17 (2.0 g, 3.02 mmol), dissolved in methanol, was added a solution of potassium hydroxide (0.95 g) in methanol (35 mL) and the reaction mixture was stirred at ambient temperature for 6 h. Most of the methanol was evaporated under vacuum, and the residue was poured into water. The aqueous reaction mixture was extracted three times with ethyl acetate. The combined ethyl acetate was washed twice with water and sodium chloride solution, and dried over sodium sulfate. Evaporation of the solvent gave a yellowish syrup. The crude material was purified on a silica gel column (3×28 cm) and eluted with ethyl acetate/hexane (35:65). Yield of pure product 18 as a white foam, 1.23 g (73%). $^1$H NMR: δ4.53–4.42 (m, 1H), 4.31–4.03 (m, 4H), 3.70–3.56 (2 m, 2H), 2.36–2.26 (broad d, 1H, J=14 Hz), 0.96 (s, 3H), 0.87 (d, 3H, J=7.5 Hz), 0.86 (s, 3H), 0.85 (s, 3H), 0.16 (s, 3H). IR: 3429, 1705, 1342, 1277, 1173, 1124, 1070, 1025 cm$^{-1}$. EIMS (m/z): 558.

EXAMPLE 6

Preparation of 7β,15βH-pyridazino [3',4',5',6':7,8,14,15]-1',2'bis(carboethoxy)-5α-cholest-3β-ol (18)

This example describes the preparation and characterization of a second compound of formula (II), 7β,15βH-pyridazino [3',4',5',6':7,8,14,15]-1',2'bis(carboethoxy)-5α-cholest-3β-ol (18), as illustrated in Scheme 6.

EXAMPLE 7

Preparation of 7β,15βH-pyridazino [3',4',5',6':7,8,14,15] -1' or 2'-carboethoxy-5α-cholest-3β-ol (19)

This example describes the preparation and characterization of a third compound of formula (II), 7β,15βH-pyridazino[3',4',5'6':7,8,14,15]-1' or 2'-carboethoxy-5α-cholest-3β-ol (19), as illustrated in Scheme 7.

21

Scheme 7

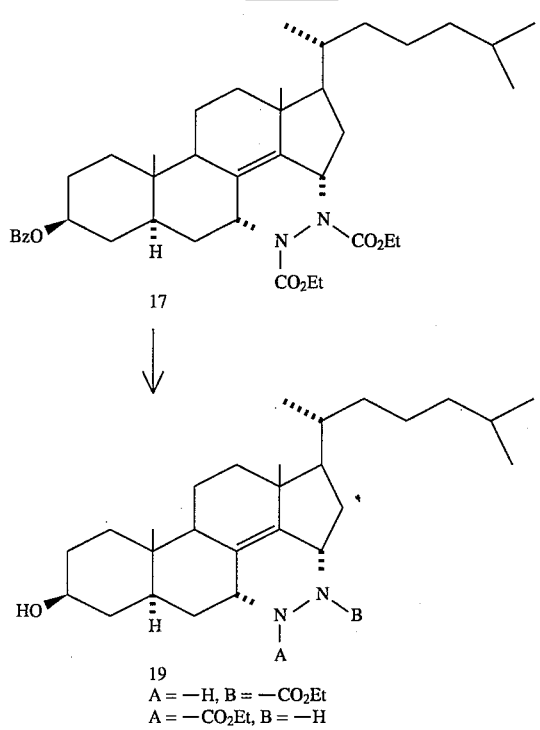

19
A = —H, B = —CO₂Et
A = —CO₂Et, B = —H

To bis(urethane) benzoate 17 (1.0 g, 1.5 mmol), dissolved in methanol (2.5 mL), was added potassium hydroxide (0.5 g) in water (0.5 mL). The reaction mixture was heated at reflux for 100 h. Most of the solvent was evaporated, and to the residue was added water. The sticky precipitate was extracted with ethyl acetate three times. The combined ethyl acetate was washed with water and dried over sodium sulfate. Evaporation of the solvent gave a crude sticky material that was purified twice by chromatography on a silica gel flash column and eluted with ethyl acetate/chloroform (3:7). Collected material was recrystallized from methanol/water to give the target compound 19 as white crystals, 0.065 g (11%), mp 110°–113° C. $^1$H NMR: δ4.41 (dddd, 1H, J=2.5, 2.5, 9.0, 9.0 Hz), 4.98 (m, 2H), 3.64–3.55 (m, 1H), 3.45–3.38 (m, 1H), 0.92 (d, 3H, J= 6.6 Hz), 0.90 (s, 3H), 0.87 (s, 3H), 0.86 (s, 3H), 0.85 (s, 3H). IR: 3534, 3356, 3212, 1702, 1674, 1410, 1304. EIMS (m/z ): 486.

EXAMPLE 8

Preparation of 7β,15βH-pyridazino [3',4',5',6':7,8,14,15]-1',2'-dimethyl-5α-cholest-3α-ol (20)

This example describes the preparation and characterization of an additional compound of formula (II), 7β,15βH-pyridazino [3',4',5',6':7,8,14,15]-1',2'-dimethyl-5α-cholest-

22

3α-ol (20), as illustrated in Scheme 8.

Scheme 8

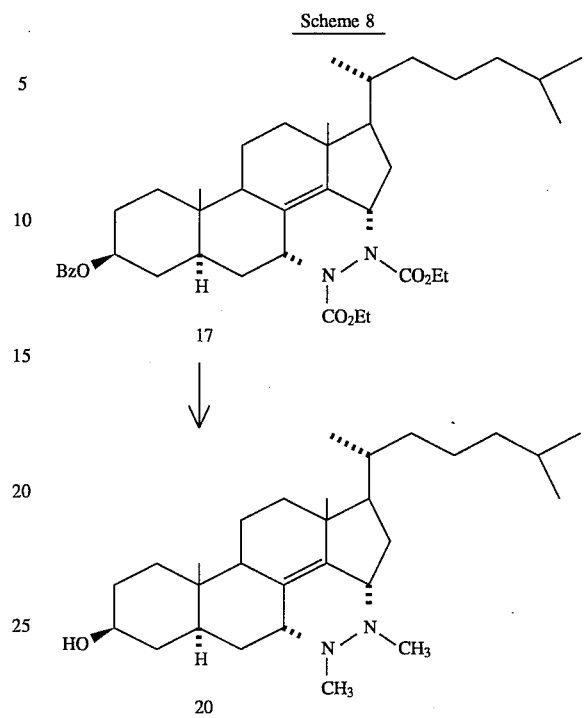

To bis(urethane) benzoate 17 (0.66 g, 1 mmol) dissolved in dry THF (10.0 mL) was added, in portions, lithium aluminum hydride (0.20 g, 5.27 mmol). The reaction mixture was stirred at ambient temperature for 6 h and, then left in the refrigerator overnight. Excess reagent was destroyed by adding water. The aluminum salt precipitated, and the THF was decanted. The inorganic salts were washed with another portion of THF. The combined organic phase was evaporated to give a thick syrup that was purified by column chromatography and eluted to give the diamine 20, 0.065 g (15%), mp 170.5°–173° C. $^1$H NMR: δ3.65–3.55 (m, 1H), 2.42 (broad s, 3H), 2.12 (broad s, 3H), 0.93 (s, 3H), 1.82 (d, 3H, J=6.1 Hz), 0.86 (d, 3H, J=6.6 Hz), 0.85 (d, 3H, J=6.6 Hz), 0.70 (s, 3H). IR: 3188, 1591, 1227, 1179, 1061, 1024 cm$^{-1}$. EIMS (m/z): 442.

EXAMPLE 9

Preparation of Benzoyloxy-7βH, 15βH-benzo [7,8,14,15]-1',2'-bis(carboethoxy)-5α-cholest-3β-ol (21)

This example describes the preparation and characterization of yet an additional compound of formula (II), benzoyloxy-7βH, 15βH-benzo[7,8,14,15]-1',2' -bis(carboethoxy)-5α-cholest-3β-ol (21), as illustrated in Scheme 9.

Scheme 9

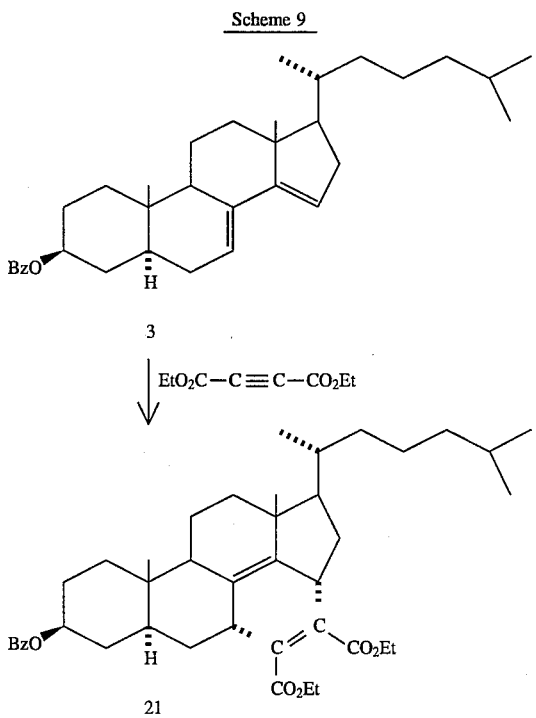

To a solution of 3 (2.44 g, 5 mmol) in benzene (30 mL) was added diethyl acetylenedicarboxylate (1.0 g, 5.88 mmol), and the reaction mixture was stirred at ambient temperature for 16 h. Starting material was still present, so another amount of diethyl acetylenedicarboxylate (0.5 g, 2.94 mmol) was added and the reaction mixture was stirred for another 8 h. The solvent was evaporated under vacuum to give the crude product as a yellow syrup that crystallized upon standing. On closer inspection on TLC, the originally formed product evidently partly aromatized from the 1,4-diene to a mixture with a small amount of aromatic compound. The two compounds that formed were separated on a preparative TLC plate (1500 μ) and was developed with ethyl acetate/hexane (1:9). Data for the product 21, mp 214°–216° C. $^1$H NMR: δ8.1–7.4 (aromatic, 5H), 5.05–4.95 (m, 1H), 4.32–4.14 (m, 4H), 3.32–3.16 (m, 2H), 1.00 (s, 3H), 0.92 (d, 3H, J=6.6 Hz), 0.87 (d, 3H, J= 6.6 Hz), 0.86 (d, 3H, J=6.7 Hz), 0.85 (s, 3H). IR: 1732, 1710, 1623, 1599, 1276, 1255, 1159, 1100, 1069, 1024 cm$^{-1}$. DCIMS (m/z): 659 (M+H), 676 (M+NH$_4$).

EXAMPLE 10

Preparation of 7βH, 15βH-Pyridazino[3',4',5',6':7,8,14,15] 5α-cholest-3β-ol-1',2'-phthalamide (23)

This example describes the preparation and characterization of yet an additional compound of formula (II), 7βH, 15βH-pyridazino-[3',4',5',6':7,8,14,15]-5α -cholest-3β-ol-1', 2'-phthalamide (23), as illustrated in Scheme 10.

Scheme 10

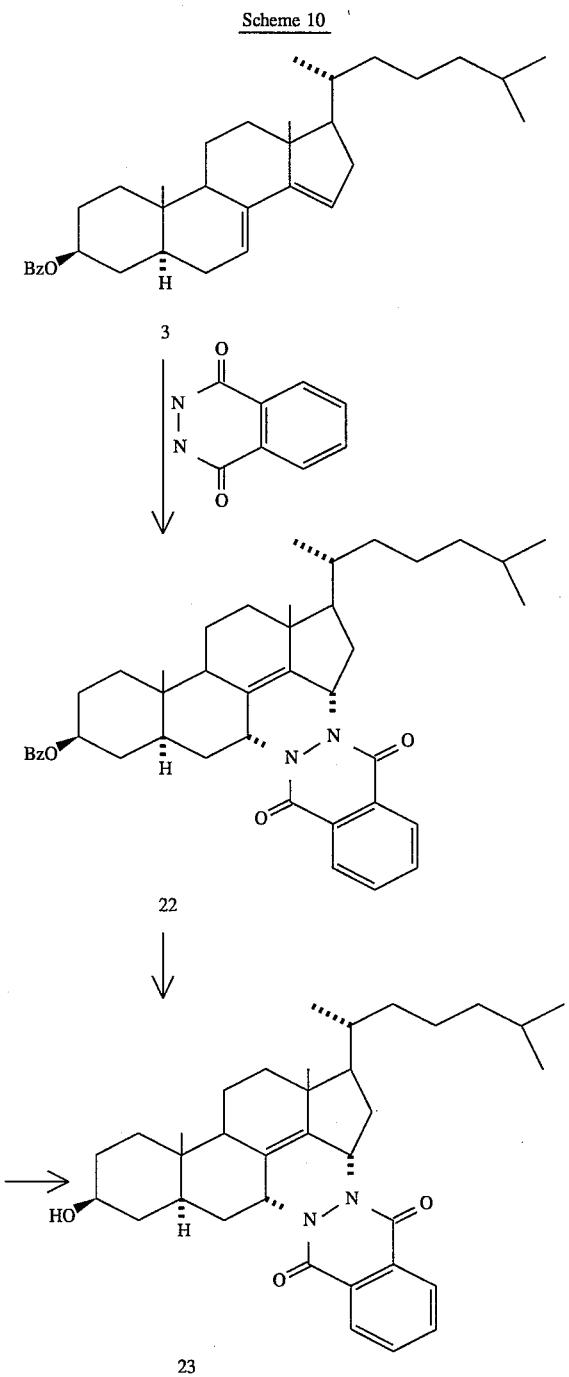

(a.) 3β-Benzoyloxy-7βH,15βH-pyridazino-[ 3',4',5',6':7, 8,14,15]-5a-cholest-1',2'-phthalamide (22)

To a stirred solution of 3 (2.44g, 5 mmol) and p-hthal-hydrazide (3.25g, 20 mmol) in dry dichloromethane (75.0 mL) cooled to 0°–5° C. was added dropwise a solution of lead tetraacetate (3.33g, 7.5 mmol) in dry dichloromethane ( 50.0 mL) and acetic acid ( 0.25 mL) . The reaction mixture was stirred at 0° C. for 2 h, whereupon TLC showed absence of starting material and only one major product. The reaction mixture was filtered through a bed of Celite, which was washed with dichloromethane. The combined filtrate was washed with water (three times, with 5% sodium bicarbonate and again water (three times), dried over sodium sulfate. Evaporation of the solvent gave a dark yellow syrup that crystallized when treated with acetone. The crude material was purified on a silica gel flash column and eluted with ethyl acetate/dichloromethane (2.5:97.5). Total yield of product 22 after crystallization from ethanol/dichloromethane, 1.69 g (52%), mp 204°–205.5° C. $^1$H NMR: δ8.26–7.42 (aromatic, 9H), 5.13–5.04 (m, 1H), 4.24 (d, 1H, J=9.5 Hz), 2.77 (dd, 1H, J=4.4, 15.4 Hz), 1.03 (s, 3H), 0.88 (d, 3H, J=6.6), 0.85 (s, 3H), 0.82 (s, 3H), 0.80 (s, 3H). IR: 1709, 1664, 1640, 1602, 1323, 1300, 1269, 1159, 1112 cm$^{-1}$. DCI MS (m/z): 649 (M+H).

(b.) 7βH,15βH-Pyridazino[3',4',5',6':7,8,14,15]-5αcholest-3β-ol-1',2'-phthalamide (23).

To a suspension of benzoate 22 (0.300g, 0.46 mmol) in methanol (4.0 mL) was added 2N potassium hydroxide (1.0 mL, 2 mmol). To the resultant viscous suspension was added THF (1.5 mL). After 2 h more potassium hydroxide (1.0 mL, 2 mmol) was added. After 48 h at ambient temperature, the reaction mixture was now homogeneous, and no starting material present by TLC. Dilute hydrochloric acid was added to adjust to pH~7. All solvent was removed, the residue was suspended in dichloromethane, and applied to a silica gel flash column. Elution with ethyl acetate/dichloromethane (1:1) yielded target compound 23, which recrystallized from ethanol/water, 0.112g (45%), mp 164°–165.5° C. $^1$H NMR: δ 8.28–8.21 (m, 2H), 7.78–7.73 (m, 2H), 5.06 (ddd, 1H, J= 3.7, 4.0, 8.1 Hz), 4.22 (d, 1H, J=9.5 Hz), 3.80–3.73 (m, 1H), 2.73 (dd, 1H, J=4.3, 15.6 Hz), 1.03 (s, 3H), 0.87 (d, 1H, J=6.6 Hz), 0.806 (d, 3H, J=6.6 Hz), 0.804 (d, 3H, J=6.6 Hz), 0.78 (s, 3H). IR: 3445, 1658, 1628, 1600, 1323, 1291 cm$^{-1}$. EIMS (m/z): 544.

EXAMPLE 11

Preparation of 3β-Benzoyloxy-benzo[7,8,14,15]-1',2'-bis(carboethoxy)-5α-cholestane (24)

This example describes the preparation and characterization of a compound of structural formula (III), 3β-benzoyloxy-benzo[7,8,14,15]-1',2'-bis(carboethoxy)-5α-cholestane (24), as illustrated in Scheme 11.

Scheme 11

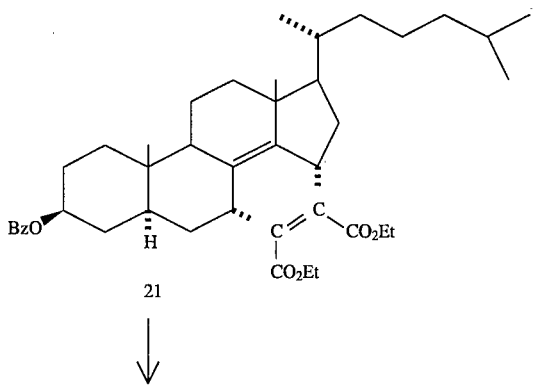

21

↓

-continued
Scheme 11

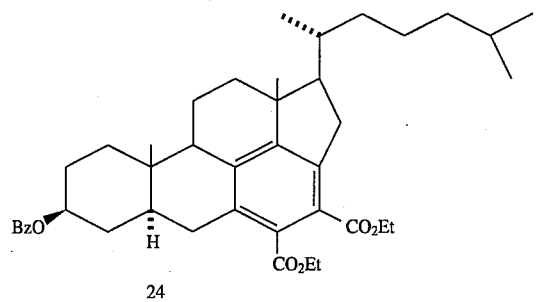

24

To a solution of 21 (0.40 g, 0.61 mmol) in dry benzene (4.0 mL) was added DDQ (0.23 g, 1.0 mmol). A precipitate formed and the reaction became a heavy slurry. TLC after 2 h showed only one component with an $R_f$ value very similar to starting material. The reaction mixture was stirred at ambient temperature for 16 h. An aliquot of the reaction mixture was purified after dilution with some dichloromethane on a TLC plate 1500 μ and developed with ethyl acetate/hexane (15:85). The strong UV absorbent band was cut out and extracted with ethyl acetate/dichloromethane. Evaporation of the solvent gave a crystalline material that was recrystallized from ethyl acetate/hexane to give white needles, mp 227°–228° C. The rest of the reaction mixture was diluted with ethyl acetate/hexane and filtered through a bed of silica gel (flash grade), then eluted with the same solvent. Evaporation of the solvent gave a crystalline crude product that was recrystallized from ethanol to give fine white needles, 0.28 g compound 24 (70%), mp 227°–228° C. $^1$H NMR: δ8.06–7.43 (aromatic, 5H), 5.05–4.95 (m, 1H), 4.40–4.25 (m, 4H), 3.25 (dd, 1H, J= 6.2, 17.0 Hz), 2.84 (dd, 1H, J=5.6, 17.6 Hz), 2.79 (dd, 1H, J=9.9, 17.6 Hz), 2.42–2.35 (m, 2H), 2.26–2.21 (m, 1H), 1.36 (t, 3H, J=7.2 Hz), 1.35 (t, 3H, J=7.2 Hz), 1.01 (d, 3H, J=5.8 Hz), 0.97 (s, 3H), 0.90 (s, 3H), 0.88 (s, 3H), 0.86 (s, 3H). IR: 1721, 1581, 1279, 1192. DCIMS: 610 (M+H-EtOH).

EXAMPLE 12

Preparation of 3β-Benzoyloxy-7α-fluoro-5α-cholest-8(14)-15-one(25)

This example describes the preparation and characterization of a compound of structural formula (IV), 3β-benzoyloxy-7α-fluoro-5α-cholest-8(14)-15-one (25), as illustrated in Scheme 12.

Scheme 12

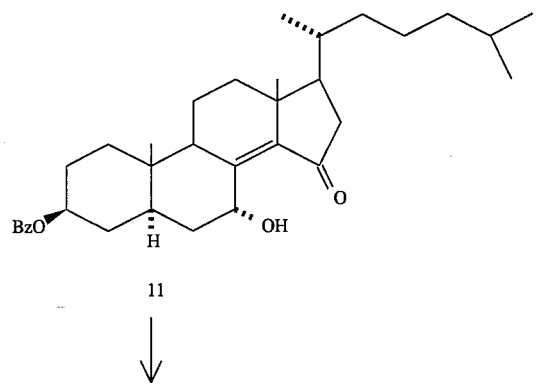

11

↓

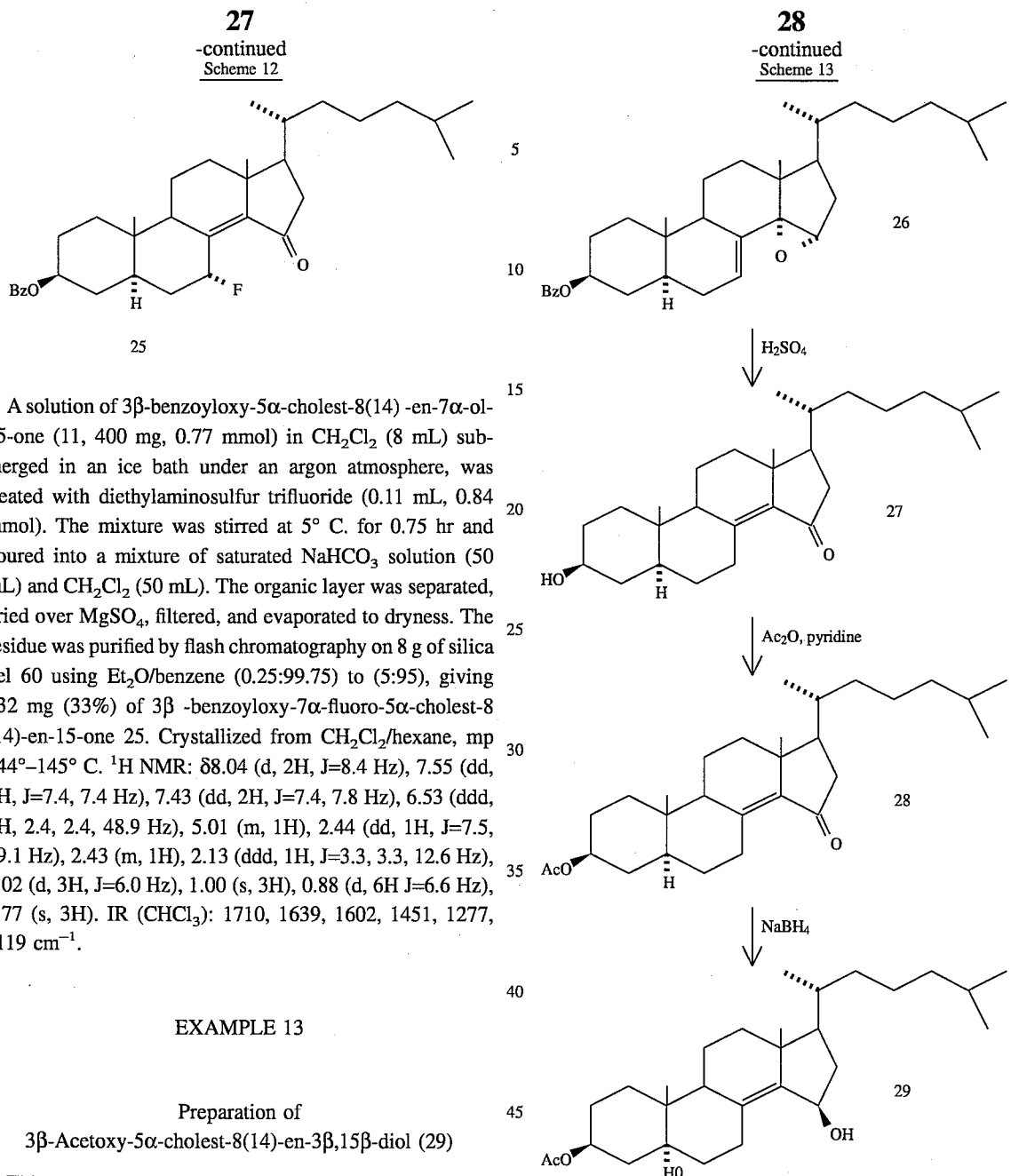

A solution of 3β-benzoyloxy-5α-cholest-8(14)-en-7α-ol-15-one (11, 400 mg, 0.77 mmol) in CH$_2$Cl$_2$ (8 mL) submerged in an ice bath under an argon atmosphere, was treated with diethylaminosulfur trifluoride (0.11 mL, 0.84 mmol). The mixture was stirred at 5° C. for 0.75 hr and poured into a mixture of saturated NaHCO$_3$ solution (50 mL) and CH$_2$Cl$_2$ (50 mL). The organic layer was separated, dried over MgSO$_4$, filtered, and evaporated to dryness. The residue was purified by flash chromatography on 8 g of silica gel 60 using Et$_2$O/benzene (0.25:99.75) to (5:95), giving 132 mg (33%) of 3β-benzoyloxy-7α-fluoro-5α-cholest-8 (14)-en-15-one 25. Crystallized from CH$_2$Cl$_2$/hexane, mp 144°–145° C. $^1$H NMR: δ8.04 (d, 2H, J=8.4 Hz), 7.55 (dd, 1H, J=7.4, 7.4 Hz), 7.43 (dd, 2H, J=7.4, 7.8 Hz), 6.53 (ddd, 1H, 2.4, 2.4, 48.9 Hz), 5.01 (m, 1H), 2.44 (dd, 1H, J=7.5, 19.1 Hz), 2.43 (m, 1H), 2.13 (ddd, 1H, J=3.3, 3.3, 12.6 Hz), 1.02 (d, 3H, J=6.0 Hz), 1.00 (s, 3H), 0.88 (d, 6H J=6.6 Hz), 0.77 (s, 3H). IR (CHCl$_3$): 1710, 1639, 1602, 1451, 1277, 1119 cm$^{-1}$.

EXAMPLE 13

Preparation of
3β-Acetoxy-5α-cholest-8(14)-en-3β,15β-diol (29)

This example describes the preparation and characterization of a compound of structural formula (V), 3β-acetoxy-5α-cholest-8(14)-en-3β,15β-diol (29), as illustrated in Scheme 13.

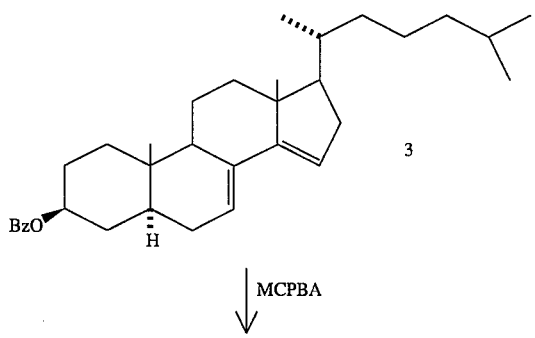

(a.) 3β-Benzoyloxy-14α,15α-epoxy-5α-cholest-7-ene (26):

To ether (1.925 L) was added 3 (50.0 g, 0.102 mol, as prepared in Example 3, part (a.)), ~95% pure and this mixture was warmed slightly to dissolve the diene 3. The solution was cooled to ambient temperature +24° C. and at that time was added, with vigorous stirring, a mixture of m-chloroperbenzoic acid (65.0 g, ~0.21 mol, Aldrich 50–60%) and sodium bicarbonate (33.0 g). Addition time was 5 min. The reaction mixture (stirred occasionally) was placed in an ice water bath and kept at 0°–5° C. for 1 h. The mixture of formed product and sodium bicarbonate was taken up on a filter and dried in vacuo. To the filter cake was added hot THF (360 mL) to dissolve the epoxide. The hot solution was filtered, and the residue on the filter was rinsed with some THF. To the clear filtrate was added hexane (720 mL). The epoxide crystallized slowly, and the flask was left at 15° C. overnight. The formed product 26 was taken up on a filter and washed with a small amount of hexane. Yield of pure product, 30.0 g (58%). NMR and IR spectra were in agreement with published data.

(b.) 3β-Hydroxy-5α-cholest-8(14)-ene-15-one (27):

A mixture of 3β-benzoyloxy-14α,15α-epoxy-5α-cholest-7-ene (26, 12.0 g, 23.8 mmol), 95% ethanol (300 mL), and water (35 mL) was cooled to 5° C. in an ice water bath. To this solution was added, in portions of 5 mL, concentrated sulfuric acid (65.0 mL). After the addition (~5 min) the reaction mixture was heated under reflux for 22 h. Stirring must be effective to prevent clumping of the starting material. The clear reaction mixture was cooled to ambient temperature, then poured into ice (700 g). A sticky precipitate was formed (could not be filtered). The water phase was extracted three times with ethyl acetate (400, 200, and 200 mL). The combined ethyl acetate phase was washed with water, 5% sodium bicarbonate, and sodium chloride solution, and dried over sodium sulfate. Evaporation of the solvent gave a semisolid yellowish compound (14 g). The crude compound 27 was purified by flash chromatography (4.0×35 cm column) and eluted with ethyl acetate/hexane (1:3). Fractions containing product were combined and evaporated to give after crystallization from methanol/water pure product as fine needles 4.5 (47%). Mp, NMR, and IR data were in agreement with published data.

(c.) 3β-Acetoxy-5α-cholest-8(14)en-3α-ol-15-one (28):

To hydroxy-enone 27 (1.2 g, 3 mmol) dissolved in dry pyridine (8.0 mL) was added dropwise acetic anhydride (2.4 mL) and the resulting mixture was stirred at ambient temperature for 16 h. To the reaction cooled in ice/water was added water (25 mL). A heavy precipitate was formed. The reaction slurry was stirred for 1 h; then the crystalline material was taken up on a filter and was washed thoroughly with water. The crystalline material was dried first in air, then under vacuum to give 1.27 (95%) of material 28 sufficiently pure to be used in the next step without further purification.

(d.) To a suspension of 28 (0.35 g, 0.79 mmol) in methanol (10 mL), cooled to 0°–5° C. was added sodium borohydride (0.30 g, 7.9 mmol). After the addition the reaction mixture was stirred at ambient temperature for 1 h. A few drops of acetic acid was added to destroy excess reagent. The reaction mixture was poured into water (30 mL) and the aqueous solution was extracted with ether three times. The combined ether solution was washed with sodium bicarbonate and sodium chloride solution, dried, and evaporated to give a colorless foam, 0.355g (100%). This material 29 was homogeneous and was used in the next example without further purification.

EXAMPLE 14

Preparation of
15β-Methoxy-5α-cholest-8(14)en-3β-ol (31)

This example describes the preparation and characterization of a second compound of formula (V), 15β-methoxy-5α-cholest-8(14)en-3β-ol (31), as illustrated in Scheme 14.

Scheme 14

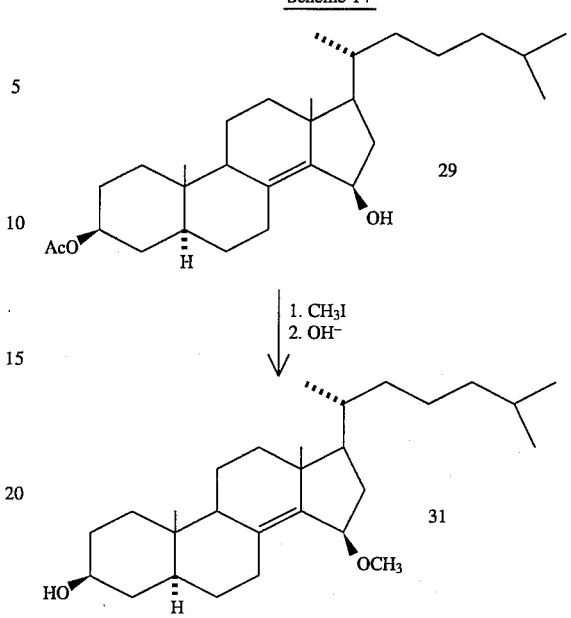

(a.) 3β-Acetoxy-15β-methoxy-5α-cholest-8(14)-ene (30):

A solution of compound (29) (0.255 g, 0.57 mmol) dissolved in dry THF (1.5 mL) was added to a suspension of potassium hydride (0.040 g, 1 mmol) in dry THF (1.5 mL). The reaction mixture was stirred for 15 min at ambient temperature; then methyl iodide (0.21g, 1.5 mmol) was added and the reaction mixture was stirred at ambient temperature for 16 h. To the reaction mixture was added water and the aqueous mixture was extracted three times with ether. The combined ether phase was washed with water and sodium chloride solution and dried over sodium sulfate. Evaporation of the solvent gave a crude mixture as a yellowish oil, which was purified on a silica gel flash column (1.5×40 cm) developed with ethyl acetate/hexane (8:92). In this manner pure 30, 0.084 g (32%) and a small amount of 3β,15β-bis-(methoxy)- 5α-cholest-8(14)-ene, were obtained. $^1$H NMR δ4.77–4.68 (m, 1H), 4.20 (dd, 1H, J=6.5, 7.6 Hz), 3.26 (s, 3H), 2.68 (ddd, 1H, J=2.0, 4.1, 13.9 Hz), 2.26 (ddd, 1H, J=8.0, 8.1, 13.2 Hz), 2.03 (s, 3H), 1.92 (m, 1H), 1.87–1.80 (m, 1H), 0.98 (s, 3H), 0.93 (d, 3H, J=6.6), 0.87 (d, 3H, J=6.7), 0.869 (d, 3H, J=6.7), 0.75 (s, 3H). EIMS (m/z): 458.

(b.) 15β-Methoxy-5α-cholest-8(14)en-3β-ol (31):

To 30 (0.070 g, 0.15 mmol) dissolved in methanol (0.8 mL) and THF (0.4 mL) was added 2N sodium hydroxide (0.2 mL) and the reaction mixture was stirred at ambient temperature for 1 h. Some starting material was still present and the reaction mixture was stirred for an additional 2 h at 50° C. To the reaction mixture was added water (~10 mL). The aqueous phase was extracted three times with ethyl acetate. The combined organic phases were washed with water and saline and dried over sodium sulfate. Evaporation of the solvent afforded a white solid that was purified on a silica gel flash column (1×10 cm) and eluted with ethyl acetate/dichloromethane (1:9). Yield of pure compound 31, 0.057 g (89%) mp 127°–128° C. $^1$H NMR: δ4.21 (dd, 1H, J= 6.5, 7.6 Hz), 3.67–3.59 (m, 1H), 3.27 (s, 3H) 2.72–2.68 (m, 1H). 2.26 (ddd, 1H, J=8.0, 8.1, 13.2 Hz), 0.98 (s, 3H), 0.93 (d, 3H, J=6.6 Hz), 0.87 (d, 3H, J=6.7), 0.867 (d, 3H, J=6.6 Hz), 0.74 (s, 3H). IR: 3263, 1336, 1283, 1212, 1131, 1092, 1041. EIMS (m/z): 416.

EXAMPLE 15
C-17 Side Chain Modifications
This example describes chemical manipulation of the side chain at the C-17 position as illustrated in Scheme 15.
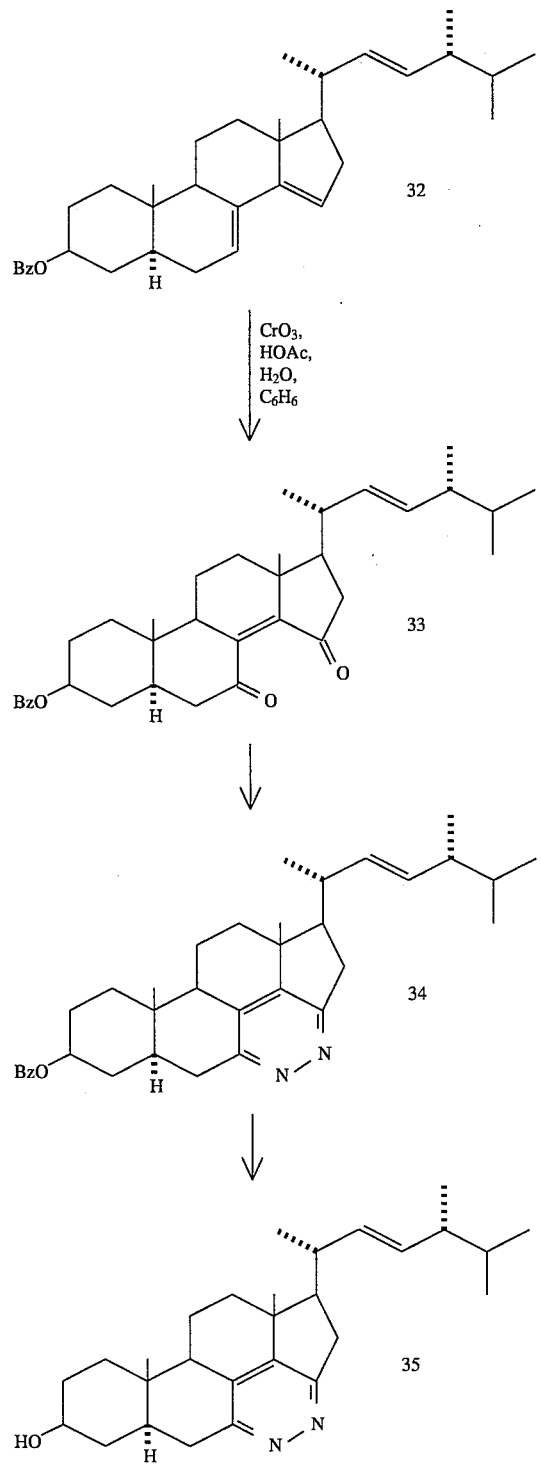

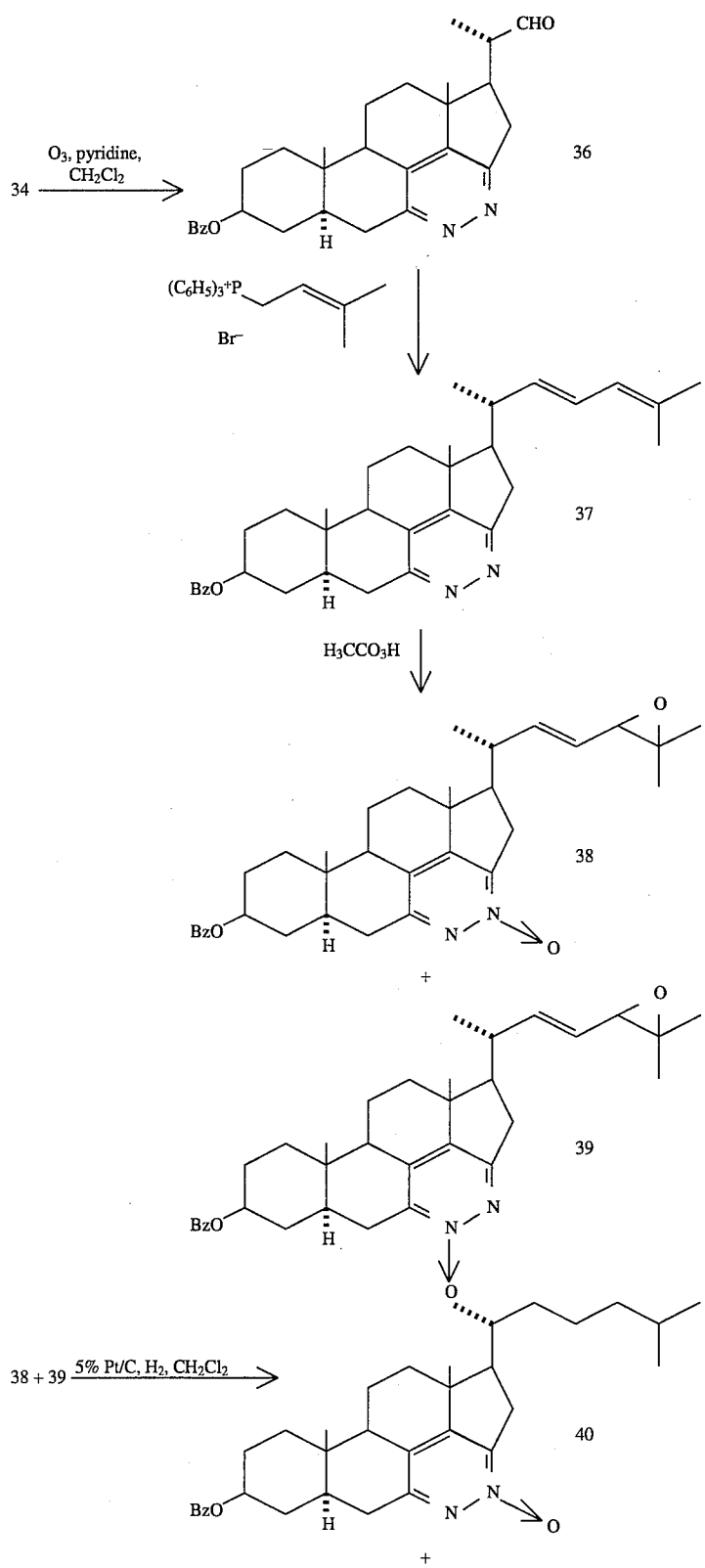

-continued
Scheme 15
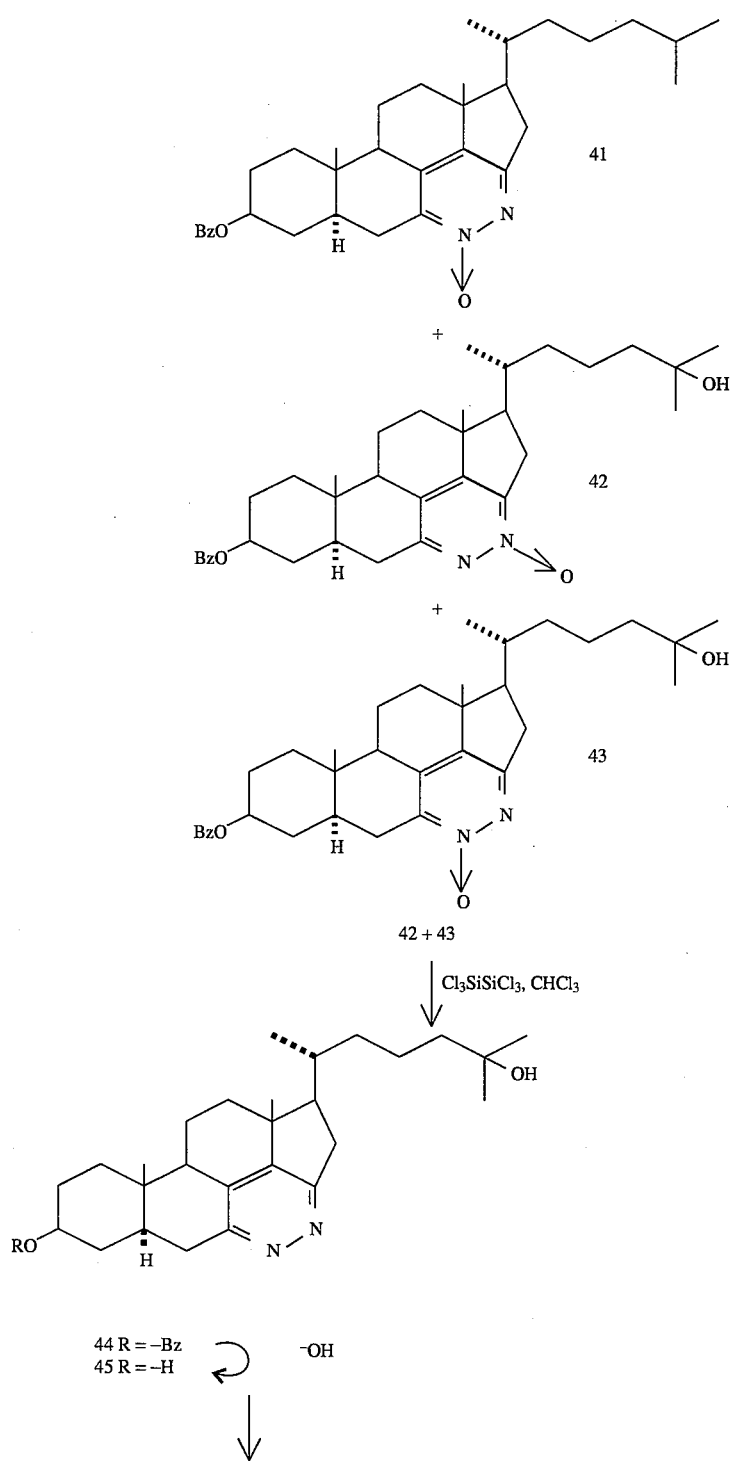
44 R = –Bz
45 R = –H

-continued
Scheme 15

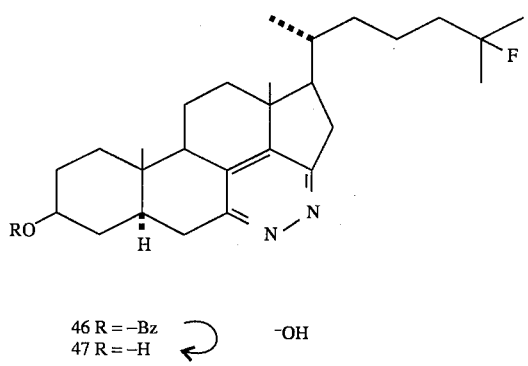

46 R = —Bz
47 R = —H      —OH (a.) 3β-Benzoyloxy-5α-ergosta-7,14-diene (32):

Compound (32) was prepared from 3β-benzoyloxy-ergosta- 5,7-diene according to the procedures of Dolle and Kruse, *J. Org. Chem.* 51:4047 (1986).

(b.) 3β-Benzoyloxy-5α-ergost-8(14)-ene-7,15-dione (3327):

A solution of 7,14,22-triene (26, 20.0 g, 0.040 mol) in benzene (375 mL) and HOAc (225 mL) was cooled in an ice bath and treated at a dropwise rate over 1.25 h with chromium trioxide (18.0 g, 0.18 mol) in HOAc (160 mL) and water (13 mL). The mixture was stirred at 5° C. for 8 h, poured into EtOAc (700 mL), and washed successively with 20% $Na_2SO_3$ (3×500 mL), saturated $NaHCO_3$ (2×500 mL), and saturated NaCl solution (500 mL). The organic layer was dried over $MgSO_4$, filtered, and evaporated, leaving 16 g of green residue. Purification by flash column chromatography on 430 g of Merck grade 60 silica gel using ether/ benzene (3:97) afforded 3.59 g (21%) of 7,15-dione (33), mp 176°–177° C. (EtOAc/Hexane). IR (Nujol): 1718, 1697, 1643, 1600, 1266, 1114 $cm^{-1}$. EIMS (m/z): 530 ($M^+$), 515 (M-Me). $^1H$ NMR: δ8.03 (d, 2H, J=8.4 Hz), 7.56 (dd, 1H, J= 7.4, 7.4 Hz), 7.44 (dd, 2H, J=7.4, 7.9 Hz), 5.29 (dd, 1H, J=7.9, 15.4 Hz), 5.16 (dd, 1H, J=8.6, 15.8 Hz), 4.98 (m, 1H), 1.11 (d, 3H, J=6.6 Hz), 1.03 (s, 3H), 1.02 (s, 3H), 0.91 (d, 3H, J=6.8 Hz), 0.84 (d, 3H, J=7.1 Hz), 0.82 (d, 3H, J=7.0 Hz).

(c.) Pyridazino[3',4',5',6':7,8,14,15]-3β -benzoyloxy-5a-ergostane (34):

To the 7,15-dione (33, 620 mg, 1.17 mmol) dissolved in EtOH (50 mL) was added anhydrous hydrazine (42 mg, 1.30 mmol) and the mixture was heated to 90° C. for 0.75 h. The solvent was evaporated under reduced pressure, and the residue was purified by flash column chromatography on 16 g of Merck grade 60 silica gel using $EtOAc/CHCl_3$ (4:6), which gave 542 mg (88%) of pyridazine (34), mp 232°–234° C. ($CH_2Cl_2$/EtOAC) . IR (Nujol): 1712, 1272, 1116 $cm^{-1}$. $^1H$ NMR: δ8.06 (d, 2H, J=8.4 Hz), 7.57 (dd, 1H, J=7.4, 7.4 Hz), 7.45 (dd, 2H, J=7.4, 7.8 Hz), 5.40 (dd, 1H, J= 8.0, 15.4 Hz), 5.25 (dd, 1H, J=8.7, 15.2 Hz), 5.04 (m, 1H), 3.22 (dd, 1H, J=5.5, 18.0 Hz), 3.00 (dd, 1H, J= 7.5, 17 Hz), 2.93 (dd, 1H, J=10.8, 16.9 Hz), 2.66 (dd, 1H, J=12.5, 17.8 Hz), 1.10 (s, 3H), 1.10 (d, 3H J=6.5 Hz), 0.97 (d, 3H, J=6.8 Hz), 0.87 (s, 3H), 0.87 (d, 3H, J=6.9 Hz), 0.85 (d, 3H, J=6.8 Hz).

(d) Pyridazino[3',4',5',6':7,8,14,15]-5α-ergostan- 3β-ol (35):

A solution of pyridazino benzoate (34, 50 mg, 0,095 mmol) in THF (2 mL) and MeOH (2 mL) was treated with 1M NaOH (0.23 mL, 0.23 mmol) and allowed to stand at ambient temperature for 14 h. The solvent was removed in vacuo, and the residue was treated with $CH_2Cl_2$ (50 mL) and washed with 10% $Na_2CO_3$ solution (50 mL). The organic layer was dried over $MgSO_4$, filtered, and evaporated, leaving 35 mg of solid. Purification by flash column chromatography on 1.7 g of Merck grade 60 silica gel yielded 29 mg (72%) of pyridazine (35), mp 194°–196° C. IR ($CHCl_3$): 3619, 1632, 1371, 1076 $cm^{-1}$. EIMS (m/z): 422 ($M^+$), 407 (M-Me). $^1H$ NMR: d 5.40 (dd, 1H, J=8.0, 15.2 Hz), 5.23 (dd, 1H, J= 8.5, 15.2 Hz), 3.71 (m, 1H), 3.23 (dd, 1H, J=5.2, 18.1 Hz), 1.09 (s, 3H), 1.09 (d, 3H, J=6.5 Hz), 0.96 (d, 3H, J= 6.8 Hz), 0.86 (d, 3H, J=6.7 Hz), 0.84 (d, 3H, J=6.7 Hz), 0.80 (s, 3H).

(e.) 3β-Benzoyloxypyridazino[3',4',5',6':7,8,14,15] -5α-pregnane-20-carboxaldehyde (36):

A solution of pyridazino [3',4',5',6':7,8,14,15] -3β-benzoyloxy-5α-ergostane (34, 3.2 g, 6.08 mmol) in $CH_2Cl_2$ (105 mL) and pyridine (1 mL) was cooled to −78° C. in a dry ice-acetone bath and ozone gas (approximately 0.95 mmol $O_3$/min) was bubbled through the solution for 25 min. Then the excess $O_3$ was removed by bubbling through argon gas. The reaction mixture was treated with methyl sulfide (3 mL) and stirred at ambient temperature for 20 min. The solvent was evaporated under reduced pressure, leaving 3.90 g of tan fluff. Purification by flash column chromatography on 77 g of Merck grade 60 silica gel using $MeOH/CHCl_3$ (2:98) yielded 1.65 g (59%) of aldehyde (36), mp 248°–252° C. EIMS (m/z): 458 ($M^+$). $^1H$ NMR: δ9.72 (d, 1H, J=2.6 Hz), 8.06 (d, 2H, J=8.3 Hz), 7.57 (dd, 1H, J=7.4, 7.4 Hz), 7.45 (dd, 2H, J=7.4, 7.9 Hz), 5.05 (m, 1H), 3.23 (dd, 1H, J=4.4, 18.7 Hz), 3.22 (dd, 1H, J=7.1, 16.4 Hz), 3.09 (dd, 1H, J=11.0, 16.4 Hz), 2.76 (ddd, 1H, J=2.6, 7.0, 10.8 Hz), 2.67 (dd, 1H, J=13.0, 17.3 Hz), 1.25 (d, 3H, J= 7.0 Hz ) , 1.13 ( s, 3H) , 0.88 ( s, 3H).

(f) Pyridazino[3',4',5',6':7,8,14,15]-3β -benzoyloxy-5α-cholesta-22,24-diene (37):

A suspension of the phosphonium bromide salt (1.18 g, 2.88 mmol) (prepared from 4-bromo-2-methyl-2-butene and $Ph_3P$) in dry THF (23 mL) at −78° C. under an argon atmosphere was treated with 1.6M n-butyllithium in hexane (1.67 mL, 2.67 mmol) and the dry ice-acetone bath was removed. The red-brown heterogeneous mixture was stirred at ambient temperature for 4 h. The reaction mixture was cooled to 5° C. and submerged in an ice bath, and aldehyde (36, 1.10 g, 2.40 mmol), dissolved in dry THF (50 mL), was added. The ice bath was removed, and the yellow mixture was stirred at ambient temperature for 2 h. The reaction mixture was diluted with $EtOAc/CH_2Cl_2$ (200 mL of 75:25), washed twice with saturated $NaC_1$ solution (200 mL each), dried over MgSO$_4$, filtered, and evaporated under reduced pressure, leaving 2.05 g of tacky tan fluff. Purification by flash column chromatography on 65 g of Merck grade 60 silica gel using acetone/CHCl$_3$ afforded 875 mg (72%) of an E/Z (7:3) mixture of diene (37).

Conversion to the E-diene was accomplished by dissolving the mixture in CH$_2$Cl$_2$ (30 mL), adding iodine (1 mg), and stirring under a fluorescent light for 1 h. The reaction mixture was washed with 10% sodium thiosulfate (50 mL), then washed with water (50 mL), and the organic layer was dried over MgSO$_4$, filtered, and evaporated, leaving 792 mg of the E-diene (37a.), mp 180°–181° C. (EtOAc). $^1$H NMR: δ8.06 (d, 2H, J=8.2 Hz), 7.57 (dd, 1H, J=7.4, 7.4 Hz), 7.45 (dd, 2H, J=7.5, 7.7 Hz), 6.28 (dd, 1H, J= 10.8, 15.4 Hz), 5.79 (d, 1H, J=10.7 Hz), 5.44 (dd, 1H, J= 8.6, 15.0 Hz), 5.04 (m, 1H), 3.19 (dd, 1H, J=5.6, 18.1 Hz), 2.97 (m, 2H), 2.65 (dd, 1H, J=12.7, 18.0 Hz), 1.77 (d, 6H, J=5.7 Hz), 1.13 (d, 3H, J=6.6 Hz), 1.11 (s, 3H) , 0.87 (s, 3H).

(g.) Peracetic Acid Epoxidation/N-Oxidation of Diene 37:

A mixture of the diene (37, 518 mg, 1.01 mmol) in CH$_2$Cl$_2$ (50 mL) containing Na$_2$CO$_3$ (1.29 g) was stirred and treated with a mixture of 32 wt% of peracetic acid (0.71 mL) in CH$_2$Cl$_2$ (20 mL) containing NaOAc.3 H$_2$O (93 mg) and stirred at ambient temperature for 2 h. The mixture was washed successively with saturated NaHCO$_3$ solution (100 mL) , 10% NaHSO$_3$ solution (100 mL) , saturated NaHCO$_3$ solution (100 mL), and water (100 mL), and the organic phase was dried over MgSO$_4$, filtered, and evaporated, leaving 611 mg of yellow fluff. Purification by flash column chromatography on 18 g of Merck grade 60 silica gel using acetone/CHCl$_3$ (1:9) Æ(2:8) gave 366 mg (67%) of a mixture of N-oxide (38) and (39). The less polar epoxy-N-oxide was isolated. DCIMS (m/z): 543 (M+H). $^1$H NMR: δ 8.06 (d, 2H, J=8.4 Hz), 7.57 (dd, 1H, J=7.4, 7.4 Hz), 7.45 (dd, 2H, J=7.3, 7.9 Hz), 5.77 (dd, 1H, J=8.9, 15.5 Hz), 5.41 (dd, 1H, J=7.6, 15.4 Hz), 5.03 (m, 1H), 3.19 (d, 1H, J=7.5 Hz), 3.08 (dd, 1H, J=6.0, 19.5 Hz), 1.58 (s, 3H), 1.37 (s, 3H), 1.30 (s, 3H), 1.15 (d, 3H, J=6.6 Hz), 1.10 (s, 3H).

The more polar epoxy-N-oxide was isolated as a white solid. $^1$H NMR: δ8.04 (d, 2H, J=8.5 Hz), 7.57 (dd, 1H, J=7.4, 7.4 Hz), 7.45 (dd, 2H, J=7.5, 7.9 Hz), 5.80 (dd, 1H, J=8.4, 15.4 Hz), 5.43 (dd, 1H, J=7.5, 15.4 Hz), 5.02 (m, 1H), 3.16), d, 1H, J=7.3 Hz), 2.92 (dd, 1H, J=5.5, 18.3 Hz), 2.81 (dd, 1H, J=10.7, 17.6 Hz), 1.36 (s, 3H), 1.29 (s, 3H), 1.13 (d, 3H, J=6.6 Hz), 1.12 (s, 3H), 0.88 (s, 3H).

(h.) Reduction of Vinyl Epoxides 38 and 39:

A mixture of the vinyl epoxides 38 and 39 (354 mg, 0.65 mmol) dissolved in CH$_2$Cl$_2$ (25 mL) containing 5% Pt/C (500 mg) was stirred under an atmosphere of hydrogen for 7 h. The catalyst was filtered off, and the solvent was removed under reduced pressure, leaving 0.351 g of crude product that was purified by flash column chromatography on 10 g of Merck grade 60 silica gel using the solvent acetone/CHCl$_3$ which gave 80 mg (22%) of the less polar 25-hydroxy-N-oxide 42 or 43. $^1$H NMR: δ8.06 (d, 2H, J=8.3 Hz), 7.57 (dd, 1H, J=7.4, 7.4 Hz), 7.45 (dd, 2H, J=7.3, 7.9 Hz), 5.03 (m, 1H), 3.08 (dd, 1H, J=5.4, 19.6 Hz), 1.24 (s, 6H), 1.07 (s, 3H), 1.02 (d, 3H, J=6.4 Hz), 0.83 (s, 3H).

The more polar 25-hydroxy-N-oxide 42 or 43 was isolated (40 mg, 11%). $^1$H NMR: δ8.05 (d, 2H, J=8.4 Hz), 7.56 (dd, 1H, J=7.4, 7.4 Hz), 7.45 (dd, 2H, J=7.4, 7.9 Hz), 5.03 (m, 1H), 3.25 (dd, 1H, J=5.4, 19.5 Hz), 1.23 (s, 6H), 1.10 (s, 3H), 1.01 (d, 3H, J=6.4 Hz), 0.88 (s, 3H).

(i) 3β-Benzoyloxy-pyridazino[3',4',5',6':7,8,14,15] -5α-cholestan-25-ol (44):

A solution of 25-hydroxy-N-oxide mixture 42 and 43 (114 mg, 0.209 mmol) in dry CHCl$_3$ (12 mL) was cooled in an ice bath under an argon atmosphere and treated with hexachlorodisilane (94 μL). After 1 h at 5° C., the reaction mixture was treated with ice (10 g) and 1N NaOH (20 mL) and CHCl$_3$ (50 mL); the layers were separated and the organic layer was dried over MgSO$_4$, filtered, and evaporated; 102 mg of residue was obtained. Purification by flash column chromatography on 2.8 g of Merck grade 60 silica gel using acetone/CHCl$_3$ (1:1) afforded 78 mg (70%) of 25-hydroxy-pyridazine 44, mp 236°–238° C. DCIMS (m/z): 531 (M+H). $^1$H NMR: δ8.05 (d, 2H, J=8.4 Hz), 7.55 (dd, 1H, J=7.4, 7.4 Hz), 7.45 (dd, 2H, J=7.4, 7.9 Hz), 5.04 (m, 1H), 1.23 (s, 6H), 1.09 (s, 3H), 1.03 (d, 3H, J=6.4 Hz), 0.88 (s, 3H).

(j) Pyridazino[3',4',5',6':7,8,14,15]-15]-5α -cholesta-3β, 25-diol (45):

a solution of the pyridazino-benzoate (44, 40 mg, 0.075 mmol) in THF (2 mL) and MeOH (4 mL) was treated with 1M NaOH (0.20 mL, 0.2 mmol) and allowed to stand at ambient temperature for 7 h. The solvent was removed under reduced pressure, and the residue was taken up in CHCl$_3$ (40 mL), washed with two portions of 10% NaCO$_3$ solution (2×30 mL), dried over MgSO$_4$, filtered, and evaporated, leaving 29 mg of residue. Purification by flash column chromatography on 2 g of Merck grade 60 silica gel using the solvent MeOH/CHCl$_3$ (8:92) afforded 22 mg (69%) of the 3β,25-diol (45), mp 229°–231° C. DCIMS (m/z): 427 (M+H). $^1$H NMR: δ 3.71 (m, 1H), 1.23 (s, 6H), 1.07 (s, 3H), 1.01 (d, 3H, J= 6.4 Hz), 0.80 (s, 3H).

(k.) 3β-Benzoyloxy-25-fluoropyridazino [3',4',5',6':7,8, 14,15]-5α-cholestane (46):

A solution of the pyridazino-25-ol (44, 38 mg, 0.072 mmol) in CH$_2$Cl$_2$ (10 mL) was cooled to −78° C. under an argon atmosphere and treated with diethylaminosulfur trifluoride (0.25 mL, 1.82 mmol). The dry ice-acetone bath was lowered, and the mixture was stirred at ambient temperature for 3 min. The reaction mixture was quenched with saturated NaHCO$_3$ solution (50 mL); then we added CH$_2$Cl$_2$ (50 ml), separated the layers, dried the organic layer over MgSO$_4$, and filtered and evaporated it under reduced pressure. The residue was purified on 2 g of Merck grade 60 flash silica gel using the solvent acetone/CHCl$_3$ (1:9), which yielded 28 mg (74%) of 25-fluoride (46), mp 197°–199° C. DCIMS (m/z): 533 (M+H). $^1$H NMR: δ8.04 (d, 2H, J=8.4 Hz), 7.55 (dd, 1H, J=7.4, 7.4 Hz), 7.45 (dd, 2H, J=7.3, 7.9 Hz), 5.05 (m, 1H), 1.42 (s, 3H), 1.32 (s, 3H) , 1.08 ( s, 3H) , 1.02 (d, 3H, J=6.4 Hz ) , 0.87 ( s, 3H).

(l.) 25-Fluoropyridazino[3',4',5',6':7,8,14,15] -5α-cholestan-3β-ol (47):

A solution of the fluorobenzoate (46, 27 mg, 0.051 mmol) in THF (2 mL) and MeOH (2 mL) was treated with 1M NaOH (0.2 mL, 0.2 mmol) and allowed to stand at ambient temperature for 7 h. After the solvent was evaporated, the residue was treated with CHCl$_3$ (40 mL) and 10% Na$_2$CO$_3$ solution (30 mL); we then separated the layers, dried the organic layer over MgSO$_4$, and filtered and evaporated it under reduced pressure. Purified on 2 g of Merck grade 60 flash silica gel using MeOH/CHCl$_3$ (5:95) afforded 13 mg (60%) of 25-fluoro-3β-ol (47), mp 196°–198° C. EIMS (m/z): 428 (M+H), 413 (M−M3). $^1$H NMR: δ3.70 (m, 1H), 1.49 (s, 3H), 1.27 (s, 3H), 1.09 (s, 3H), 1.02 (d, 3H, J=6.4 Hz), 0.81 (s, 3H).

EXAMPLE 16

Biological Testing (a.) In Vitro Assay for Inhibition of Cholesterol Biosynthesis in CHO Cells:

Chinese Hamster ovary (CHO) cells were seeded at $1\times10^5$ cells per 60-mm Petri dish and incubated at 37° C. in F-12 medium supplemented with fetal calf serum (5%). After 24 h, the medium was aspirated and replaced with delipidated calf serum in F-12 medium containing the test compounds. At various concentrations, either ethanol or dimethyl sulfoxide was used to dissolve the test compounds to a final concentration of 0.1% in the cell medium. Controls contained the vehicle alone. After incubation for 16–18 h, $^{14}$C-acetate (20 μM final concentration) was added and incubation continued for 5.5 h. Cells were placed on ice and washed three times with cold 0.85% saline. The cells were then scraped off the plates with a rubber policeman into saline (2 mL). An aliquot for protein was taken, and the remainder of the cell suspension was centrifuged at 800×g for 10 min. The supernatant was discarded and the pellet extracted by vortexing 15 s in chloroform:methanol (2 mL of 2:1). The chloroform extract was washed twice; 0.73% aq. NaCl (0.4 mL) was added, vortexed, and centrifuged, and the top layer was discarded. A portion of the upper phase mixture of chloroform:methanol:water (0.4 mL of 3:48:47) was added and gently swirled to avoid mixing with the bottom layer. The resultant samples were centrifuged, and the top layer was discarded. The procedure was repeated before methanol was finally added to combine the two layers and the solvent was evaporated. Chloroform (200 μL) was added to the residue and an aliquot (150 μL) taken. To the aliquot was added cholesterol (40 μg in 20 μL), and the samples were concentrated. The lipids were dissolved in chloroform (50 μL) and spotted on silica gel G thin-layer chromatography plates. After development in hexane:ether:acetic acid (80:20:1), the $^{14}$C-cholesterol spot was located with iodine vapor and scraped into a scintillation vial, and the radioactivity was counted with a scintillation counter. Results are set forth in Table 1.

TABLE 1

| In Vitro Inhibition of Cholesterol Biosynthesis | |
|---|---|
| Compound | IC$_{50}$ (μM) |
| (25-Hydroxycholesterol) | 0.35 |
|  | 1.4 |
|  | 1.6 |

TABLE 1-continued
In Vitro Inhibition of Cholesterol Biosynthesis
| Compound | IC$_{50}$ (µM) |
| --- | --- |
| 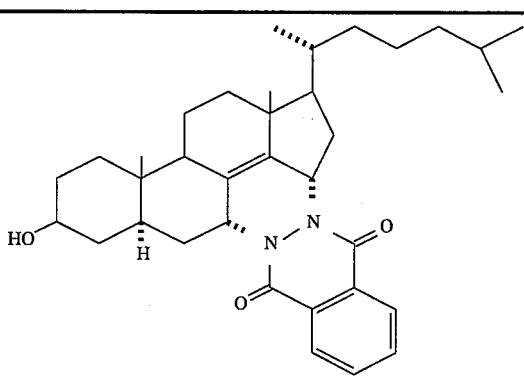 | 2.1 |
| 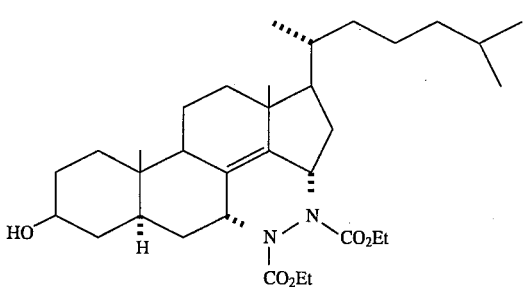 | 0.8 |
| 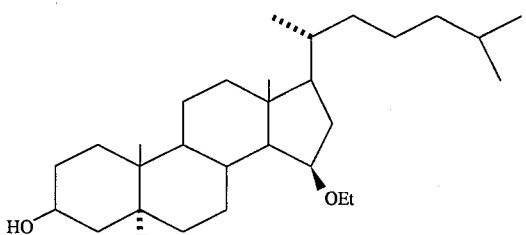 | 4.0 |
| 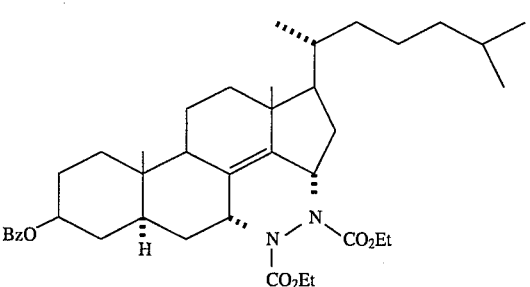 | 1.3 |
| 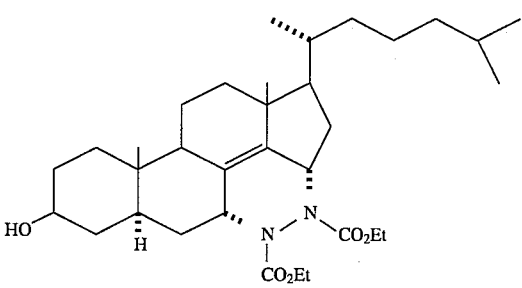 | 0.8 |

TABLE 1-continued
In Vitro Inhibition of Cholesterol Biosynthesis
| Compound | IC$_{50}$ (µM) |
|---|---|
| 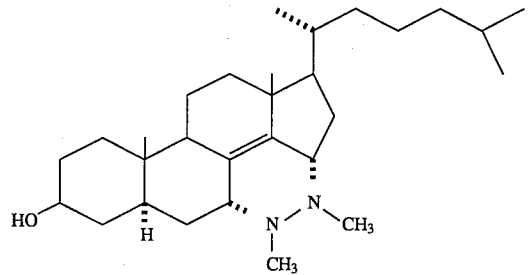 | 1.6 |
| 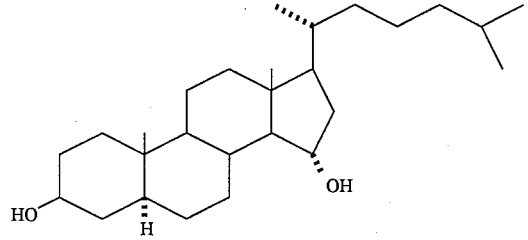 | 0.36 |
| 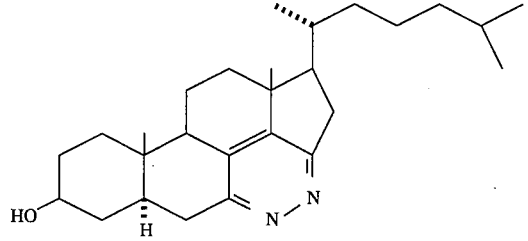 | 0.09 |
| 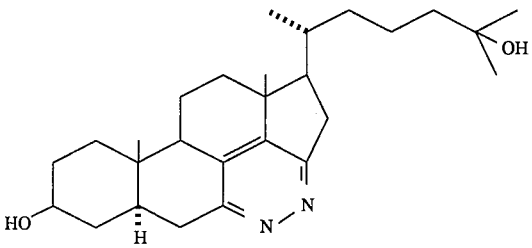 | 3.4 |
| 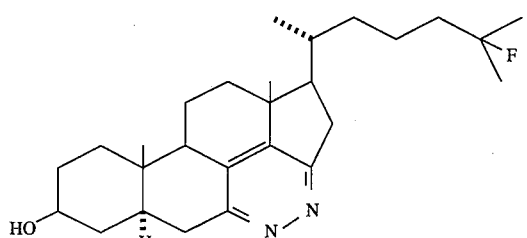 | 0.16 |
| 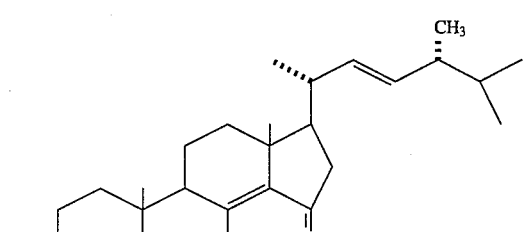 | 0.11 |

TABLE 1-continued

In Vitro Inhibition of Cholesterol Biosynthesis

| Compound | IC$_{50}$ (µM) |
|---|---|
| (steroid structure with HO–, 5α-H, C=N in ring) | 0.05 |
| (steroid structure with HO–, 5α-H, C=O, 15-OH, Δ8,14) | 1.1 |
| (steroid structure with BzO–, 5α-H, C=O, 15-OH, Δ8,14) | 3.5 |
| (steroid structure with HO–, 5α-H, 15-ketone) | 0.2 |
| (steroid structure with HO–, 5α-H, 15-OMe, Δ8,14) | 0.9 |
| (steroid structure with BzO–, 5α-H, 7-F, 15-ketone, Δ8,14) | 0.2 |

TABLE 1-continued

In Vitro Inhibition of Cholesterol Biosynthesis

| Compound | IC$_{50}$ (μM) |
|---|---|
| 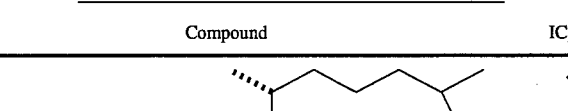 | <0.25 |

(b.) In Vivo Cholesterol Biosynthesis Inhibition in Rats with Oral Administration of Test Compounds:

Male Sprague-Dawley rats weighing 120 to 150 g were used. The animals were placed on a cholesterol-free diet immediately upon arrival and housed in a room with a reverse light cycle. One week after they had adapted to the light cycle, the experiment was begun by gavaging the animals three times daily with various amounts of test compound 13 suspended in 1.0 mL of saline. The control group received 1.0 mL of saline alone. On the seventh day of the experiment, sodium [1-$^{14}$C] acetate (20 μCi/rat) was injected intraperitoneally 30 min after the oral administration (gavage) of test compounds and 2 h before the mid-dark point in the diurnal cycle; 4 h after the $^{14}$C-acetate injection, the animals were killed and blood samples were collected after decapitation. Plasma was obtained by centrifuging blood in an EDTA-treated centrifuge tube at 3000 rpm for 10 min. Cholesterol synthesis was measured by determining the level of $^{14}$C-labeled nonsaponifiable lipid present in 1.0 mL of plasma; 1.0 mL of plasma was first mixed with 1.0 mL of saline, followed by 5.0 mL of 10% KOH in absolute ethanol. Samples were saponified at 75° C. for 1 h. After cooling, 44,000 dpm, 0.5 nmol of [1,2-$^{3}$H] cholesterol was added to each sample as an internal standard for calculating recovery through the extraction procedure. Samples were extracted once with 5 mL of petroleum ether, and the organic phase was backwashed with 5 mL of saline. The extracts were dried on a nitrogen evaporator, and the residue was reconstituted into 0.5 mL of CHCl$_3$-MeOH (2:1). The 0.5-mL reconstituted samples were transferred into counting vials containing 2 mL of ethanol, and both $^{3}$H and $^{14}$C were counted in 10 mL of scintillation fluid. The $^{3}$H-cholesterol internal standard recovery value from each sample was used to correct each sample to 100% recovery of $^{14}$C-cholesterol. The total cholesterol level and HDL in each plasma sample was also measured. The comparison between test groups and the control group was evaluated for both cholesterol levels and $^{14}$C-acetate incorporation. Results are set forth in Table 2.

TABLE 2

Effect of Pyridazine (13) on Cholesterol Levels and $^{14}$C-Acetate Incorporation in Plasma of Rats After Three Daily Doses via Gavage for Seven Days

| Dose[a] | Cholesterol Levels[b] | | $^{14}$C-Acetate Incorporation | |
|---|---|---|---|---|
| | Total | HDL | cpm/ml | Inhibition |
| 0.16 | 66.8 ± 3.4 | 44.0 ± 10.6 | 696 ± 107 | 42% |
| 0.33 | 62.6 ± 2.4 | 27.6 ± 3.5 | 510 ± 122 | 58% |
| 1.0 | 61.4 ± 3.0 | 28.6 ± 1.9 | 385 ± 47 | 68% |
| 3.0 | 60.8 ± 0.9 | 28.8 ± 4.3 | 383 ± 38 | 69% |
| 7.5 | 44.0 ± 1.0 | 14.3 ± 0.33 | 340 ± 50 | 72% |
| C[c] | 77.6 ± 2.3 | 32 ± 2.1 | 1200 ± 95 | — |

[a]Mg/rat/day.
[b]Mg/100 ml, mean ± S.E.
[c]Control.

(c.) Assay for Lowering Cholesterol Levels in Rats with Oral Administration of Test Compound 15:

The experiment was carried out as described in (b.). However, in this experiment, blood was drawn on days 0, 3 and 7. Total cholesterol levels and HDL were measured on these blood samples. Results are shown in Table 3.

TABLE 3

Effect of Pyridine (15) on Cholesterol Levels in Plasma of Rats After Three Daily Doses via Gavage for Seven Days

| Dose, mg/rat/day[a] | Cholesterol Levels[b] | |
|---|---|---|
| | Day 0 | |
| | Total | HDL |
| 0.16 | 94.8 ± 5.5 | 39.6 ± 2.06 |
| 0.33 | 99.0 ± 3.7 | 35.8 ± 1.91 |
| 1.0 | 88.8 ± 7.78 | 37.8 ± 3.01 |
| 3.0 | 85.6 ± 6.57 | 35.2 ± 3.14 |
| Control | 95.8 ± 9.79 | 42.2 ± 4.40 |
| | Day 3 | |
| | Total | HDL |
| 0.16 | 83.6 ± 3.56 | 36.4 ± 1.36 |
| 0.33 | 75.6 ± 1.94 | 35.8 ± 2.40 |
| 1.0 | 78.8 ± 2.86 | 34.4 ± 1.69 |
| 3.0 | 72.2 ± 2.95 | 29.6 ± 0.98 |
| Control | 85.2 ± 2.95 | 41.6 ± 2.62 |

TABLE 3-continued

Effect of Pyridine (15) on Cholesterol
Levels in Plasma of Rats After
Three Daily Doses via Gavage for Seven Days

| Dose, mg/rat/day[a] | Cholesterol Levels[b] | |
|---|---|---|
| | Day 7 | |
| | Total | HDL | the cholesterol-free diet with no restriction. The food consumption and body weights of all groups were recorded daily. Blood samples were taken from all groups on day 0 and every third or fourth day throughout the entire experiment. Plasma was obtained by drawing blood into EDTA-treated centrifuge tubes and centrifuging at 3000 rpm for 10 min. The total cholesterol level and HDL in each plasma sample were determined using a Gemini autoanalyzer. Results are set forth in Table 4:

TABLE 4

EFFECT OF ORALLY ADMINISTERED INHIBITORS ON CHOLESTEROL LEVELS IN PLASMA OF RATS (mg/100 mL), MEAN ± S.E.

| Group | Inhibitor | Day 0 | | Day 4 | | Day 7 | | Day 10 | |
|---|---|---|---|---|---|---|---|---|---|
| | | Total | LDL | Total | LDL | Total | LDL | Total | LDL |
| 1 | 15-ketone[a] 27 | 74 ± 3 | 34 ± 2 | 69 ± 2 | 31 ± 2 | 48 ± 4[b] | 23 ± 2 | 66 ± 2 | 41 ± 1.5 |
| 2 | Pair-fed group 1 | 80 ± 2 | 36 ± 1.8 | 82 ± 2 | 32 ± 2 | 67 ± 3 | 20 ± 1 | 67 ± 3 | 35 ± 1.4 |
| 3 | Pyridazine[a] 13 | 74 ± 1 | 34 ± 1.8 | 62 ± 2 | 28 ± 2 | 46 ± 3[b,c] | 17 ± 3 | 47 ± 5 | 29 ± 2 |
| 4 | Pair-fed group 3 | 76 ± 3 | 31 ± 2 | 79 ± 5 | 32 ± 2 | 58 ± 3 | 21 ± 2 | 59 ± 4 | 35 ± 2 |
| 5 | Control | 70 ± 1 | 29 ± 0.9 | 77 ± 2 | 28 ± 2 | 76 ± 4 | 26 ± 2 | 81 ± 3 | 32 ± 1.5 |

[a]Rats were fed cholesterol-free diet containing 0.2% of inhibitors throughtout the experiment. Pair-fed groups were allowed to consume the same amount of cholesterol-free diet without the test compound as their counterpart experimental groups. The control group was allowed free access to the cholesterol-free diet with no restriction.
[b]Significantly lower than cholesterol level on Day 0 (P < 0.001); also significantly lower than that of the pair-fed group (P < 0.005) and control group (P < 0.001) on Day 7.
[c]Significantly lower than that of the pair-fed group (P < 0.02).

TABLE 3-continued

Effect of Pyridine (15) on Cholesterol
Levels in Plasma of Rats After
Three Daily Doses via Gavage for Seven Days

| Dose, mg/rat/day[a] | Cholesterol Levels[b] | |
|---|---|---|
| 0.16 | 69.4 ± 3.66 | 39.8 ± 1.02 |
| 0.33 | 57.6 ± 2.89 | 36.0 ± 2.55 |
| 1.0 | 58.0 ± 4.06 | 25.0 ± 1.87 |
| 3.0 | 46.4 ± 2.23 | 15.4 ± 1.40 |
| Control | 84.8 ± 4.40 | 49.6 ± 4.01 |

[a]Mg/rat/day.
[b]Mg/100 mL, mean ± S.E.

(d.) Assay for Lowering Cholesterol Levels in Rats Fed Drug-Containing Food Ad Libitum:

Male Sprague-Dawley rats weighing 150 to 200 g were used for this experiment. The animals were divided into groups of six rats each. All groups were kept on a cholesterol-free diet throughout the entire experiment. This diet was prepared by adding the test compound in small portions (usually 100 mg) to 100 g of choleserol-free diet in a 1-liter glass separatory funnel with a stopper. The diet was thoroughly mixed after each addition of the test compound. The resulting diet was kept in a refrigerator at all times. Before feeding, the diet was allowed to warm to room temperature. The animals were housed individually in metabolic cages. All test groups were allowed free access to the cholesterol-free diet containing the proper doses of the test compound. A pair-fed group was assigned to each test group and allowed free access to the cholesterol-free diet only in the amount consumed by its corresponding counterpart on the previous day. The control group was allowed free access to

We claim:
1. A compound having the structural formula (I)

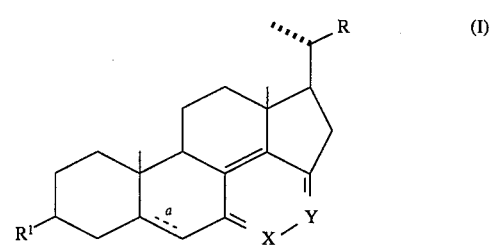

wherein:

R is selected from the group consisting of $CH_3$, $CH_2OH$, $CH_2CH_2CH_2CH(CH_3)_2$, $CH_2CH_2CH_2C(CH_3)_2$ —OH, $CH_2CH_2CH_2C(CH_3)_2$—F, $CH=CH$—$CH(CH_3)$— $CH(CH_3)_2$, $CH_2CH_2CH(CH_2CH_3)CH(CH_3)_2$, and $CH=CH$— $CH(CH_2CH_3)CH(CH_3)_2$;

$R^1$ is selected from the group consisting of —OH, =O, —$OR^8$, —$O(CO)R^9$, —$O(CO)$—$(CH_2)_n$—COOH, a sulfate group, or an Mg, Na, or K salt of a sulfate group, where $R^8$ is lower alkyl, $R^9$ is a $C_1$–$C_{20}$ aliphatic group or phenyl, and n is an integer in the range of 2 to 6 inclusive;

X and Y may be the same or different, and are selected from the group consisting of N, N→O, CH, C—OH, C—$OCH_3$ and C—Z where Z is halogen, with the proviso that at least one of X and Y is N or N→O; and a represents either a single bond or a double bond, with the proviso that if X and Y are both N, R is other than $CH=CH$—$CH(CH_3)$—$CH(CH_3)_2$.

2. The compound of claim 1, wherein X is N and Y is selected from the group consisting of CH, C—OH, C—OCH$_3$ and C—Z.

3. The compound of claim 1, wherein X is selected from the group consisting of CH, C—OH, C—OCH$_3$ and C—Z, and Y is N.

4. The compound of claim 1, wherein X and Y are both N.

5. The compound of claim 1, wherein R is CH$_2$CH$_2$CH$_2$CH(CH$_3$)$_2$.

6. The compound of claim 1, wherein R$^1$ is hydroxyl or benzoate.

7. The compound of claim 1, wherein:
R is CH$_2$CH$_2$CH$_2$CH(CH$_3$)$_2$;
R$^1$ is hydroxyl or benzoate;
X and Y are both N; and
a represents a single bond.

8. A compound having the structural formula (II)

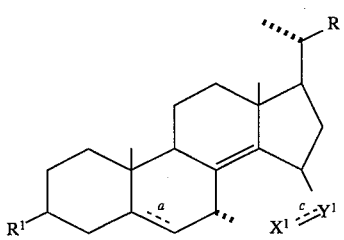
(II)

wherein:
R is selected from the group consisting of CH$_3$, CH$_2$OH, CH$_2$CH$_2$CH$_2$CH(CH$_3$)$_2$, CH$_2$CH$_2$CH$_2$C(CH$_3$)$_2$—OH, CH$_2$CH$_2$CH$_2$C(CH$_3$)$_2$—F, and CH=CH—CH(CH$_3$)—CH(CH$_3$)$_2$, CH$_2$CH$_2$CH(CH$_2$CH$_3$)CH(CH$_3$)$_2$, and CH=CH—CH(CH$_2$CH$_3$)CH(CH$_3$)$_2$;

R$^1$ is selected from the group consisting of —OH, =O, —OR$^8$, —O(CO)R$^9$, —O(CO)—(CH$_2$)$_n$—COOH, a sulfate group, or an Mg, Na, or K salt of a sulfate group, where R$^8$ is lower alkyl, R$^9$ is a C$_1$–C$_{20}$ aliphatic group or phenyl, and n is an integer in the range of 2 to 6 inclusive;

X$^1$ and Y$^1$ are independently selected from the group consisting of NR$^2$, CR$^2$, O and S where the R$^2$ may be the same or different and are selected from the group consisting of H, lower alkyl and —COOR$^3$ where R$^3$ is lower alkyl, or wherein the R$^2$ are linked together to form a —(CO)—Z—(CO)—bridge, where Z is alkylene, alkenylene, phenylene having up to four ring substituents, —S—, or —NR$^{10}$— where R$^{10}$ is H, lower alkyl or phenyl having up to 5 ring substituents, and wherein the ring substituents are selected from the group consisting of —NH$_2$, —COOH, —NO$_2$, halogen and lower alkyl, with the proviso that X$^1$ and Y$^1$ are not both CR$^2$;

R$^2$ is selected from the group consisting of H, lower alkyl and —COOR$^3$ where R$^3$ is lower alkyl; and a represents either a single bond or a double bond.

9. The compound of claim 8, wherein R is CH$_2$CH$_2$CH$_2$CH(CH$_3$)$_2$.

10. The compound of claim 9, wherein X$^1$ and Y$^1$ are both NR$^2$.

11. The compound of claim 10, wherein R$^2$ and R$^3$ are both lower alkyl.

12. The compound of claim 11, wherein R$^2$ and R$^3$ are both methyl.

13. The compound of claim 10, wherein R$^2$ and R$^3$ are both —COOC$_2$H$_5$.

14. The compound of claim 8, wherein R$^1$ is hydroxyl or benzoate.

15. The compound of claim 9, wherein R$^1$ is hydroxyl or benzoate.

16. The compound of claim 10, wherein R$^1$ is hydroxyl or benzoate.

17. The compound of claim 8, wherein a represents a single bond.

18. A pharmaceutical composition for lowering serum cholesterol, comprising, in combination with a pharmaceutically acceptable carrier, an effective serum cholesterol lowering amount of a compound having the structural formula (I)

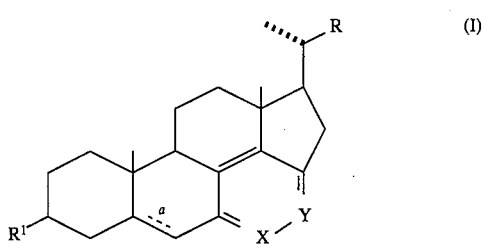
(I)

wherein:
R is selected from the group consisting of CH$_3$, CH$_2$OH, CH$_2$CH$_2$CH$_2$CH(CH$_3$)$_2$, CH$_2$CH$_2$CH$_2$C(CH$_3$)$_2$—OH, CH$_2$CH$_2$ CH$_2$C(CH$_3$)$_2$—F, CH=CH—CH(CH$_3$)—CH(CH$_3$)$_2$, CH$_2$CH$_2$CH(CH$_2$CH$_3$)CH(CH$_3$)$_2$, and CH=CH—CH(CH$_2$CH$_3$)CH(CH$_3$)$_2$;

R$^1$ is selected from the group consisting of —OH, =O, —OR$^8$, —O(CO)R$^9$, —O(CO)—(CH$_2$)$_n$—COOH, a sulfate group, or an Mg, Na, or K salt of a sulfate group, where R$^8$ is lower alkyl, R$^9$ is a C$_1$–C$_{20}$ aliphatic group or phenyl, and n is an integer in the range of 2 to 6 inclusive;

X and Y may be the same or different, and are selected from the group consisting of N, N→O, CH, C—OH, C—OCH$_3$ and C—Z where Z is halogen, with the proviso that at least one of X and Y is N or N→O; and a represents either a single bond or a double bond.

19. The composition of claim 18, wherein X is N and Y is selected from the group consisting of CH, C—OH, C—OCH$_3$ and C—Z.

20. The composition of claim 18, wherein X is selected from the group consisting of CH, C—OH, C—OCH$_3$ and C—Z, and Y is N.

21. The composition of claim 18, wherein X and Y are both N.

22. The composition of claim 18, wherein R is CH$_2$CH$_2$CH$_2$CH(CH$_3$)$_2$.

23. The composition of claim 18, wherein:
R is CH$_2$CH$_2$CH$_2$CH(CH$_3$)$_2$;
R$^1$ is hydroxyl or benzoate;
X and Y are both N; and
a represents a single bond.

24. A pharmaceutical composition for lowering serum cholesterol, comprising, in combination with a pharmaceutically acceptable carrier, an effective serum cholesterol lowering amount of a compound having the structural formula (II)

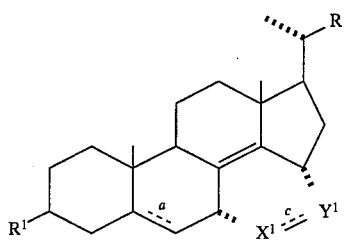

wherein:
R is selected from the group consisting of $CH_3$, $CH_2OH$, $CH_2CH_2CH_2CH(CH_3)_2$, $CH_2CH_2CH_2C(CH_3)_2$—OH, $CH_2CH_2CH_2C(CH_3)_2$—F, and $CH=CH-CH(CH_3)-CH(CH_3)_2$, $CH_2CH_2CH(CH_2CH_3)CH(CH_3)_2$, and $CH=CH-CH(CH_2CH_3)CH(CH_3)_2$;

$R^1$ is selected from the group consisting of —OH, =O, —$OR^8$, —$O(CO)R^9$, —O(CO)—$(CH_2)_n$—COOH, a sulfate group, or an Mg, Na, or K salt of a sulfate group, where $R^8$ is lower alkyl, $R^9$ is a $C_1$–$C_{20}$ aliphatic group or phenyl, and n is an integer in the range of 2 to 6 inclusive;

$X^1$ and $y^1$ are independently selected from the group consisting of $NR^2$, $CR^2$, O and S, where the $R^2$ may be the same or different and are selected from the group consisting of H, lower alkyl and —$COOR^3$ where $R^3$ is lower alkyl, or wherein the $R^2$ are linked together to form a —(CO)—Z—(CO)—bridge, where Z is alkylene, alkenylene, phenylene having up to four ring substituents, —S—, or —$NR^{10}$— where $R^{10}$ is H, lower alkyl or phenyl having up to 5 ring substituents, and wherein the ring substituents are selected from the group consisting of —$NH_2$, —COOH, —$NO_2$, halogen and lower alkyl, with the proviso that $X^1$ and $Y^1$ are not both $CR^2$;

$R^2$ is selected from the group consisting of H, lower alkyl and —$COOR^3$ where $R^3$ is lower alkyl; and a represents either a single bond or a double bond.

25. The composition of claim 24, wherein R is $CH_2CH_2CH_2CH(CH_3)_2$.

26. The composition of claim 25, wherein $X^1$ and $Y^1$ are both $NR^2$.

27. The composition of claim 26, wherein $R^2$ and $R^3$ are both lower alkyl.

28. The composition of claim 27, wherein $R^2$ and $R^3$ are both methyl.

29. The composition of claim 26, wherein $R^2$ and $R^3$ are both —$COOC_2H_5$.

30. A method for lowering serum cholesterol level in a warm-blooded mammal, comprising administering to such mammal an effective serum cholesterol lowering amount of a compound having the structural formula (I)

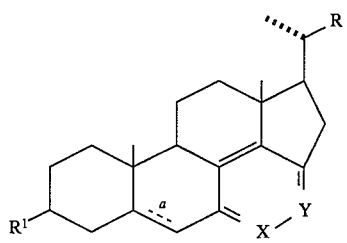

wherein:
R is selected from the group consisting of $CH_3$, $CH_2OH$, $CH_2CH_2CH_2CH(CH_3)_2$, $CH_2CH_2CH_2C(CH_3)_2$—OH, $CH_2CH_2CH_2C(CH_3)_2$—F, $CH=CH-CH(CH_3)-CH(CH_3)_2$, $CH_2CH_2CH(CH_2CH_3)CH(CH_3)_2$, and $CH=CH-CH(CH_2CH_3)CH(CH_3)_2$;

$R^1$ is selected from the group consisting of —OH, =O, —$OR^8$, —O(CO) $R^9$, —O(CO)—$(CH_2)_n$—COOH, a sulfate group, or an Mg, Na, or K salt of a sulfate group, where $R^8$ is lower alkyl, $R^9$ is a $C_1$–$C_{20}$ aliphatic group or phenyl, and n is an integer in the range of 2 to 6 inclusive;

X and Y may be the same or different, and are selected from the group consisting of N, N→O, CH, C—OH, C—$OCH_3$ and C—Z where Z is halogen, with the proviso that at least one of X and Y is N or N→O; and a represents either a single bond or a double bond.

31. A method for lowering serum cholesterol level in a warm-blooded mammal, comprising administering to such mammal an effective serum cholesterol lowering amount of a compound having the structural formula (II)

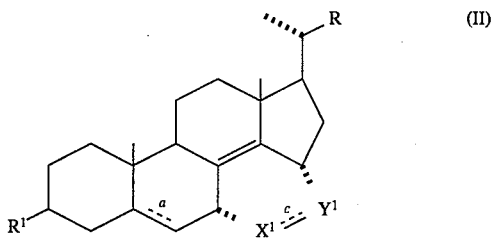

wherein:
R is selected from the group consisting of $CH_3$, $CH_2OH$, $CH_2CH_2CH_2CH(CH_3)_2$, $CH_2CH_2CH_2C(CH_3)_2$—OH, $CH_2CH_2CH_2C(CH_3)_2$—F, and $CH=CH-CH(CH_3)-CH(CH_3)_2$, $CH_2CH_2CH(CH_2CH_3)CH(CH_3)_2$, and $CH=CH-CH(CH_2CH_3)CH(CH_3)_2$;

$R^1$ is selected from the group consisting of —OH, =O, —$OR^8$, —$O(CO)R^9$, —O(CO)—$(CH_2)_n$—COOH a sulfate group, or an Mg, Na, or K salt of a sulfate group, where $R^8$ is lower alkyl $R^9$ is a $C_1$–$C_{20}$ aliphatic group or phenyl, and n is an integer in the range of 2 to 6 inclusive;

$X^1$ and $y^1$ are independently selected from the group consisting of $NR^2$, $CR^2$, O and S where the $R^2$ may be the same or different and are selected from the group consisting of H, lower alkyl and —$COOR^3$ where $R^3$ is lower alkyl, or wherein the $R^2$ are linked together to form a —(CO)—Z—(CO)—bridge, where Z is alkylene, alkenylene, phenylene having up to four ring substituents, —S—, or —$NR^{10}$— where $R^{10}$ is H, lower alkyl or having up to 5 ring substituents, and wherein the ring substituents are selected from the group consisting of —$NH_2$, —COOH, —$NO_2$, halogen and lower alkyl, with the proviso that $X^1$ and $Y^1$ are not both $CR^2$;

$R^2$ is selected from the group consisting of H, lower alkyl and —$COOR^3$ where $R^3$ is lower alkyl; and a represents either a single bond or a double bond.

* * * * *